(12) United States Patent
Borody

(10) Patent No.: US 10,617,724 B2
(45) Date of Patent: *Apr. 14, 2020

(54) COMPOSITIONS FOR FECAL FLORAL TRANSPLANTATION AND METHODS FOR MAKING AND USING THEM AND DEVICES FOR DELIVERING THEM

(71) Applicant: CRESTOVO HOLDINGS LLC, Somerville, MA (US)

(72) Inventor: Thomas Borody, Five Dock (AU)

(73) Assignee: Crestovo Holdings LLC, Somerville, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/557,283

(22) Filed: Aug. 30, 2019

(65) Prior Publication Data

US 2019/0381114 A1 Dec. 19, 2019

Related U.S. Application Data

(63) Continuation of application No. 16/523,726, filed on Jul. 26, 2019, and a continuation of application No. 16/433,437, filed on Jun. 6, 2019, now Pat. No. 10,463,702, and a continuation of application No. 16/433,437, filed on Jun. 6, 2019, now Pat. No. 10,463,702, which is a continuation of application No. 16/364,144, filed on Mar. 25, 2019, which is a continuation of application No. 16/118,400, filed on Aug. 30, 2018, now Pat. No. 10,278,997, which is a continuation of application No. 15/975,456, filed on May 9, 2018, which is a continuation of application No. 15/950,939, filed on Apr. 11, 2018, now Pat. No. 10,064,899, which is a continuation of application No. 15/782,519, filed on Oct. 12, 2017, now Pat. No. 9,962,413, which is a continuation of application No. 15/093,679, filed on Apr. 7, 2016, now Pat. No. 10,022,406, which is a continuation of application No. 13/813,915, filed as application No.
(Continued)

(30) Foreign Application Priority Data

Aug. 4, 2010 (AU) ................................ 2010903474

(51) Int. Cl.
| | | |
|---|---|---|
| A61K 35/74 | (2015.01) | |
| A61K 35/24 | (2015.01) | |
| A61K 9/48 | (2006.01) | |
| C12N 1/00 | (2006.01) | |
| A61P 1/12 | (2006.01) | |
| A61M 5/142 | (2006.01) | |
| A61K 35/742 | (2015.01) | |
| A61K 35/00 | (2006.01) | |
| A61M 31/00 | (2006.01) | |
| A61B 10/00 | (2006.01) | |

(52) U.S. Cl.
CPC ............ *A61K 35/74* (2013.01); *A61K 9/4891* (2013.01); *A61K 35/24* (2013.01); *A61K 35/742* (2013.01); *A61M 5/142* (2013.01); *A61P 1/12* (2018.01); *C12N 1/00* (2013.01); *A61B 10/0038* (2013.01); *A61K 9/4875* (2013.01); *A61K 2035/115* (2013.01); *A61M 31/00* (2013.01)

(58) Field of Classification Search
None
See application file for complete search history.

(56) References Cited

U.S. PATENT DOCUMENTS

| | | | |
|---|---|---|---|
| 3,192,116 | A | 6/1965 | Möse et al. |
| 3,320,130 | A | 5/1967 | Henry |

(Continued)

FOREIGN PATENT DOCUMENTS

| | | |
|---|---|---|
| AU | 2001276160 B2 | 6/2007 |
| CA | 1333564 | 12/1994 |

(Continued)

OTHER PUBLICATIONS

"Autoimmune Disease List," *American Autoimmune Related Diseases Association*, pp. 1-4 (2017) <https://www.aarda.org/diseaselist/>.
"Certain infectious and parasitic diseases (A00-B99)," *International Statistical Classification of Diseases and Related Health Problems, 10th Revision (ICD-10)—WHO Version*, Chapter 1, pp. 1 (2016) <www.apps.who.int/classifications/icd10/browse/2016/en#/I>.
"Spore-Forming Gram-Positive Bacilli: *Bacillus* and *Clostridium* Species," *Jawetz, Melnick, & Adelberg's Medical Microbiology*, 26th Edition, Chapter 11, pp. 1-15 (2012).
"ARGF—'Autologous Rehabilitation of Gastrointestinal Flora,'" Medipex Report for Medilink NW, pp. 1-42, n.d., Web, Feb. 10, 2012 <http://www.bacteriotherapy.org/docs/medipex-report.pdf>.

(Continued)

*Primary Examiner* — Michelle F. Paguio Frising
(74) *Attorney, Agent, or Firm* — David Marsh; Scott Douglas; Arnold & Porter Kaye Scholer LLP

(57) ABSTRACT

In alternative embodiments, the invention provides compositions, e.g., formulations, used for gastric, gastrointestinal and/or colonic treatments or lavage, e.g., orthostatic lavage, e.g., for inducing the purgation (e.g., cleansing) of a gastrointestinal (GI) tract, including a colon; and methods for making and using them. In alternative embodiments, compositions and methods of the invention are used for the stabilization, amelioration, treatment and/or prevention of constipation, for the treatment of abdominal pain, particularly non-specific abdominal pain, and diarrhea, including diarrhea caused by a drug side effect, a psychological condition, a disease or a condition such as Crohn's Disease, a poison, a toxin or an infection, e.g., a toxin-mediated traveler's diarrhea, or *C. difficile* or the pseudo-membranous colitis associated with this infection. In alternative embodiments, the invention provides pharmaceuticals and products (articles) of manufacture for delivering these compositions and formulations to an individual, e.g., a human or an animal. The invention also provides devices for delivering a fecal material to a patient.

32 Claims, 2 Drawing Sheets

Related U.S. Application Data

PCT/AU2011/000987 on Aug. 4, 2011, now Pat. No. 9,308,226.

(60) Provisional application No. 61/494,363, filed on Jun. 7, 2011, provisional application No. 61/483,487, filed on May 6, 2011, provisional application No. 61/451,087, filed on Mar. 9, 2011, provisional application No. 61/450,099, filed on Mar. 7, 2011.

(56) References Cited

U.S. PATENT DOCUMENTS

| | | |
|---|---|---|
| 3,713,836 A | 1/1973 | Carlsson |
| 3,913,564 A | 10/1975 | Freshley |
| 4,098,728 A | 7/1978 | Rosenblatt |
| 4,309,782 A | 1/1982 | Paulin |
| 4,332,790 A | 6/1982 | Sozzi et al. |
| 4,335,107 A | 6/1982 | Snoeyenbos et al. |
| 4,452,779 A | 6/1984 | Cockerill |
| 4,536,409 A | 8/1985 | Farrell et al. |
| 4,657,762 A | 4/1987 | Mikkola et al. |
| 4,710,379 A | 12/1987 | Kawai et al. |
| 4,892,731 A | 1/1990 | Arai et al. |
| 4,975,286 A | 12/1990 | Hechter |
| 5,213,807 A | 5/1993 | Chemburkar et al. |
| 5,266,315 A | 11/1993 | Taguchi et al. |
| 5,443,826 A | 8/1995 | Borody |
| 5,599,795 A | 2/1997 | McCann et al. |
| 5,728,380 A | 3/1998 | Allen et al. |
| 5,800,821 A | 9/1998 | Acheson et al. |
| 5,837,238 A | 11/1998 | Casas et al. |
| 5,858,356 A | 1/1999 | Wolf et al. |
| 5,902,578 A | 5/1999 | Halpin-Dohnalek et al. |
| 5,902,743 A | 5/1999 | Luchansky et al. |
| 6,087,386 A | 7/2000 | Chen et al. |
| 6,162,464 A | 12/2000 | Jacob et al. |
| 6,245,740 B1 | 6/2001 | Goldenberg et al. |
| 6,284,274 B1 | 9/2001 | Merrill et al. |
| 6,428,783 B1 | 8/2002 | Khachatrian et al. |
| 6,479,051 B1 | 11/2002 | Bruce |
| 6,514,531 B1 | 2/2003 | Alaux et al. |
| 6,645,530 B1 | 11/2003 | Borody |
| 6,649,397 B1 | 11/2003 | Nakamura |
| 6,756,032 B1 | 6/2004 | Tepper et al. |
| 6,926,907 B2 | 8/2005 | Plachetka |
| 6,979,674 B1 | 12/2005 | Goldenberg et al. |
| 6,984,513 B2 | 1/2006 | Brown et al. |
| 7,018,629 B2 | 3/2006 | Jacob et al. |
| 7,374,753 B1 | 5/2008 | Farmer et al. |
| 7,541,091 B2 | 6/2009 | Sisson et al. |
| 7,749,509 B2 | 7/2010 | Cobb et al. |
| 7,763,276 B1 | 7/2010 | Shodai et al. |
| 7,799,341 B2 | 9/2010 | Porzio et al. |
| 7,815,956 B2 | 10/2010 | Lee et al. |
| 7,846,475 B2 | 12/2010 | Shiraishi et al. |
| 7,888,062 B1 | 2/2011 | Garner et al. |
| 7,998,510 B2 | 8/2011 | Caswell |
| 8,168,171 B2 | 5/2012 | Mogna et al. |
| 8,460,648 B2 | 6/2013 | Borody |
| 8,586,029 B2 | 11/2013 | Kasper et al. |
| 8,637,297 B2 | 1/2014 | Fernandez et al. |
| 8,658,153 B2 | 2/2014 | Daube et al. |
| 8,771,673 B2 | 7/2014 | Cobb et al. |
| 9,040,036 B2 | 5/2015 | Borody |
| 9,050,358 B2 | 6/2015 | Borody |
| 9,308,226 B2 | 4/2016 | Borody |
| 9,320,763 B2 | 4/2016 | Borody |
| 9,408,872 B2 | 8/2016 | Borody |
| 9,468,658 B2 | 10/2016 | Borody |
| 9,572,841 B2 | 2/2017 | Borody |
| 9,572,842 B2 | 2/2017 | Borody |
| 9,610,308 B2 | 4/2017 | Borody |
| 9,623,056 B2 | 4/2017 | Borody |
| 2001/0014322 A1 | 8/2001 | Chen et al. |
| 2002/0013270 A1 | 1/2002 | Bolte |
| 2002/0022019 A1 | 2/2002 | Laulund |
| 2002/0039599 A1 | 4/2002 | Lin et al. |
| 2003/0092163 A1 | 5/2003 | Collins et al. |
| 2003/0092724 A1 | 5/2003 | Kao et al. |
| 2003/0147858 A1 | 8/2003 | Renaud et al. |
| 2004/0062757 A1 | 4/2004 | Finegold |
| 2004/0167062 A1 | 8/2004 | Bolte |
| 2004/0170617 A1 | 9/2004 | Finegold |
| 2004/0223956 A1 | 11/2004 | Naidu et al. |
| 2006/0076536 A1 | 4/2006 | Barshied |
| 2006/0099197 A1 | 5/2006 | Farmer |
| 2006/0115465 A1 | 6/2006 | Macfarlane et al. |
| 2006/0177424 A1 | 8/2006 | Cobb et al. |
| 2006/0275223 A1 | 12/2006 | Burr |
| 2007/0059296 A1 | 3/2007 | Chen |
| 2008/0254009 A1 | 10/2008 | Finegold |
| 2008/0299197 A1 | 12/2008 | Toneguzzo et al. |
| 2010/0112003 A1 | 5/2010 | Collins et al. |
| 2010/0178349 A1 | 7/2010 | Kolter et al. |
| 2010/0178413 A1 | 7/2010 | Gorris |
| 2010/0184785 A1 | 7/2010 | Kolter et al. |
| 2010/0222311 A1 | 9/2010 | Thommes et al. |
| 2010/0226866 A1 | 9/2010 | Yamashiro et al. |
| 2010/0233278 A1 | 9/2010 | Ookawa et al. |
| 2010/0239667 A1 | 9/2010 | Hemmingsen et al. |
| 2010/0247489 A1 | 9/2010 | Saur-Brosch et al. |
| 2010/0247665 A1 | 9/2010 | Takahashi |
| 2010/0255231 A1 | 10/2010 | Chau et al. |
| 2010/0255307 A1 | 10/2010 | Gonze et al. |
| 2010/0278930 A1 | 11/2010 | Okumura et al. |
| 2010/0285164 A1 | 11/2010 | Schaible et al. |
| 2010/0289164 A1 | 11/2010 | Porzio et al. |
| 2010/0297031 A1 | 11/2010 | Ubeda Perez et al. |
| 2011/0008554 A1 | 1/2011 | Chen et al. |
| 2011/0045222 A1 | 2/2011 | Peters |
| 2011/0081320 A1 | 4/2011 | Westall et al. |
| 2011/0200570 A1 | 8/2011 | Mosbaugh et al. |
| 2011/0218216 A1 | 9/2011 | Vivek et al. |
| 2012/0020941 A1 | 1/2012 | Wacklin et al. |
| 2012/0039853 A1 | 2/2012 | Corveleyn et al. |
| 2012/0064133 A1 | 3/2012 | Chauhan et al. |
| 2012/0087895 A1 | 4/2012 | Mazmanian et al. |
| 2012/0183612 A1 | 7/2012 | Brogmann et al. |
| 2012/0252775 A1 | 10/2012 | Finegold |
| 2013/0045274 A1 | 2/2013 | Hlavka |
| 2013/0195804 A1 | 8/2013 | Borody |
| 2013/0259899 A1 | 10/2013 | Allen-Vercoe et al. |
| 2013/0316394 A1 | 11/2013 | Stimpson |
| 2014/0065132 A1 | 3/2014 | Hsiao et al. |
| 2014/0086877 A1 | 3/2014 | Hlavka |
| 2014/0147417 A1 | 5/2014 | Sadowsky et al. |
| 2014/0147425 A1 | 5/2014 | Henn et al. |
| 2014/0234260 A1 | 8/2014 | Borody |
| 2014/0255351 A1 | 9/2014 | Berstad et al. |
| 2014/0328803 A1 | 11/2014 | McKenzie et al. |
| 2014/0341921 A1 | 11/2014 | Honda et al. |
| 2014/0342438 A1 | 11/2014 | Allen-Vercoe et al. |
| 2014/0363397 A1 | 12/2014 | Allen-Vercoe et al. |
| 2015/0050246 A1 | 2/2015 | Jones et al. |
| 2015/0093360 A1 | 4/2015 | McKenzie et al. |
| 2015/0143557 A1 | 5/2015 | Honda et al. |
| 2015/0152484 A1 | 6/2015 | Krajmalnik-Brown et al. |
| 2015/0190435 A1 | 7/2015 | Henn et al. |
| 2015/0224152 A1 | 8/2015 | Littman et al. |
| 2015/0238545 A1 | 8/2015 | Borody |
| 2015/0238546 A1 | 8/2015 | Borody |
| 2015/0297642 A1 | 10/2015 | Borody |
| 2015/0306144 A1 | 10/2015 | Borody |
| 2015/0306155 A1 | 10/2015 | Borody |
| 2015/0306156 A1 | 10/2015 | Borody |
| 2015/0374761 A1 | 12/2015 | Sadowsky et al. |
| 2016/0089363 A1 | 3/2016 | Borody |
| 2016/0151429 A1 | 6/2016 | Borody |
| 2016/0151431 A1 | 6/2016 | Borody |
| 2016/0151432 A1 | 6/2016 | Borody |
| 2016/0151433 A1 | 6/2016 | Borody |
| 2016/0158294 A1 | 6/2016 | Von Maltzahn et al. |
| 2016/0279178 A1 | 9/2016 | Borody |

(56) References Cited

U.S. PATENT DOCUMENTS

| | | |
|---|---|---|
| 2016/0279179 A1 | 9/2016 | Borody |
| 2016/0339065 A1 | 11/2016 | Adams et al. |
| 2017/0216378 A1 | 8/2017 | Honda et al. |

FOREIGN PATENT DOCUMENTS

| | | |
|---|---|---|
| CA | 2 391 422 A1 | 1/2004 |
| CN | 1561387 A | 1/2005 |
| CN | 101496819 A | 8/2009 |
| CN | 201441672 U | 4/2010 |
| DE | 2 134 179 A1 | 1/1973 |
| EP | 0 303 426 A2 | 2/1989 |
| EP | 0 456 418 A2 | 11/1991 |
| EP | 0 433 299 B1 | 5/1998 |
| EP | 1 514 572 A2 | 3/2005 |
| EP | 1 514 572 A3 | 11/2006 |
| EP | 1 800 688 A1 | 6/2007 |
| EP | 1 514 572 B1 | 12/2008 |
| EP | 2 823 822 B1 | 10/2016 |
| FR | 1275 M | 5/1962 |
| FR | 2427 M | 3/1964 |
| FR | 2828 M | 10/1964 |
| FR | 5528 M | 11/1967 |
| FR | 2 244 464 A1 | 4/1975 |
| GB | 1 271 674 A | 4/1972 |
| JP | 64-67192 | 3/1989 |
| JP | H05-306221 A | 11/1993 |
| JP | H07-242539 A | 9/1995 |
| JP | H07-242557 A | 9/1995 |
| JP | 3 144 556 B2 | 3/2001 |
| JP | 2004-501095 | 1/2004 |
| JP | 2005-118544 A | 5/2005 |
| JP | 2008-106066 | 5/2008 |
| JP | 2010-513359 | 4/2010 |
| JP | 2010-520234 A | 6/2010 |
| KR | 10-0913405 B1 | 8/2009 |
| WO | WO 90/01335 A1 | 2/1990 |
| WO | WO 95/33046 A1 | 12/1995 |
| WO | WO 96/11014 A1 | 4/1996 |
| WO | WO 98/13068 A1 | 4/1998 |
| WO | WO 00/07571 A2 | 2/2000 |
| WO | WO 00/015760 | 3/2000 |
| WO | WO 00/42168 A2 | 7/2000 |
| WO | WO 02/07741 A1 | 1/2002 |
| WO | WO 03/033681 A2 | 4/2003 |
| WO | WO 2005/017095 A2 | 2/2005 |
| WO | WO 2006/127355 A2 | 11/2006 |
| WO | WO 2008/077614 A2 | 7/2008 |
| WO | WO 2008/105715 A2 | 9/2008 |
| WO | WO 2008/117266 A2 | 10/2008 |
| WO | WO 2008/117267 A2 | 10/2008 |
| WO | WO 2008/077614 A3 | 1/2009 |
| WO | WO 2009/024429 A2 | 2/2009 |
| WO | WO 2009/026306 A2 | 2/2009 |
| WO | WO 2009/055362 A1 | 4/2009 |
| WO | WO 2010/040020 A1 | 4/2010 |
| WO | WO 2011/033310 A1 | 3/2011 |
| WO | WO 2011/094027 A1 | 8/2011 |
| WO | WO 2011/110347 A2 | 9/2011 |
| WO | WO 2011/151941 A1 | 12/2011 |
| WO | WO 2011/152566 A1 | 12/2011 |
| WO | WO 2012/013861 A2 | 2/2012 |
| WO | WO 2012/045150 A1 | 4/2012 |
| WO | WO 2012/016287 A3 | 11/2012 |
| WO | WO 2013/090825 A1 | 6/2013 |
| WO | WO 2014/078911 A1 | 5/2014 |
| WO | WO 2014/152338 A1 | 9/2014 |
| WO | WO 2014/152484 A1 | 9/2014 |
| WO | WO 2015/006355 A2 | 1/2015 |
| WO | WO 2015/051323 A1 | 4/2015 |
| WO | WO 2015/077794 A1 | 5/2015 |
| WO | WO 2015/095241 A2 | 6/2015 |
| WO | WO 2016/133450 A1 | 2/2016 |
| WO | WO 2017/075098 A1 | 5/2017 |
| WO | WO 2017/152137 A2 | 9/2017 |

OTHER PUBLICATIONS

"Frequently Asked Questions about Clostridium difficile for Healthcare Providers," Healthcare-associated Infections (HAIs), Centers for Disease Control and Prevention, pp. 1-6, Nov. 25, 2010, updated Mar. 6, 2012, Web, May 19, 2014 <http://www.cdc.gov/HAI/organisms/cdiff/Cdiff_faqs_HCP.html>.

"Functional Anatomy of Prokaryotic and Eukaryotic Cells," printed Mar. 16, 2017 <http://classes.midlandstech.edu/carterp/courses/bio225/chap04/lecture2.htm>.

"Monilia," Def. 1, Stedman's Medical Dictionary, n.d., Web, Nov. 22, 2005.

"Probiotic," Def. 1, MSN Encarta—Dictionary, Encarta, n.d., Web, Dec. 1, 2005.

Aas et al., "Recurrent Clostridium difficile Colitis: Case Series Involving 18 Patients Treated with Donor Stool Administered via a Nasogastric Tube," *Clinical Infectious Diseases*, 36(5):580-585 (2003).

Abrams, "Open-Label, Uncontrolled Trial of Bowel Sterilization and Repopulation with Normal Bowel Flora for Treatment of Inflammatory Bowel Disease," *Current Therapeutic Research*, 58(12):1001-1012 (1997).

Acha et al., "Changes of viability and composition of the *Escherichia coli* flora in faecal samples during long time storage," Journal of Microbiological Methods, Elsevier, 63(3):229-238 (2005).

Agrawal et al., "'Global warming' to *Mycobacterium avium* subspecies *paratuberculosis*," *Future Microbiol*, 9(7):829-832 (2014), in U.S. Appl. No. 15/093,679.

Agrawal et al., "A Long-Term Follow-Up Study of the Efficacy and Safety of Fecal Microbiota Transplant (FMT) for Recurrent/Severe/Complicated *C. difficile* Infection (CDI) in the Elderly," *Gastroenterol*, 146(5)(Suppl 1):S42-43 (2014).

Aitken et al., "Demonstration of Intracellular *Mycobacterium* Species in Crohn's Disease Using Novel Technologies," Poster Presentation—2015 ACG Annual Scientific Meeting, Honolulu, Hawaii, USA (2015).

Akao et al., "A Purgative Action of Barbaloin Is Induced by *Eubacterium* sp. Strain BAR, a Human Intestinal Anaerobe, Capable of Transforming Barbaloin to Aloe-Emodin Anthrone," Biol. Pharm., 19(1):136-138 (1996).

Al-Eidan et al., "Clostridium difficile-associated diarrhoea in hospitalised patients," *J. Clin. Pharm. Ther.*, 25(2):101-109 (2000).

Al-Nassir et al., "Comparison of Clinical and Microbiological Response to Treatment of Clostridium difficile-Associated Disease with Metronidazole and Vancomycin," *Clin Infect Dis.*, 47(1):56-62 (2008).

Anand et al., "Epidemiology, clinical manifestations, and outcome of Clostridium difficile-associated diarrhea," *Am J Gastroenterol.*, 89(4):519-23 (1994).

Ananthakrishnan et al., "Excess hospitalisation burden associated with Clostridium difficile in patients with inflammatory bowel disease," *Gut*, 57(2):205-210 (2007).

Anderson et al., "Systematic review: faecal microbiota transplantation in the management of inflammatory bowel disease," *Aliment. Pharmacol. Ther.*, 36:503-16 (2012).

Andoh et al., "Terminal restriction fragment polymorphisum analyses of fecal microbiota in five siblings including two with ulcerative colitis," *Journal of Clinical Gastroenterology*, 2:343-345 (2009).

Andrews et al., "'Putting back the bugs': Bacterial Treatment Relieves Chronic Constipation and Symptoms of Irritable Bowel Syndrome," *Med. J. Aust.*, 159(9):633-634 (1993).

Andrews et al., "Bacteriotherapy for Chronic Constipation—A Long Term Follow-Up," *Gastroenterol*, 108:A563 Abstract (1995).

Andrews et al., "Chronic Constipation (CC) may be reversed by Bacteriotherapy," *Gastroenterol*, 106:A459 (1994).

Andrews et al., "Chronic constipation reversed by restoration of bowel flora. A case and a hypothesis," *European Journal of Gastroenterology & Hepatology*, 4:245-247 (1992).

Anorexia nervosa, Encyclopedia Index A, healthAtoZ, Medical Network, Inc., pp. 1-7, n.d., Web, Nov. 23, 2005 <http://www.healthatoz.com/healthatoz/Atoz/ency/anorexia_nervosa.jsp>.

Arkkila et al., "Fecal Bacteriotherapy for Recurrent *Clostridium difficile* Infection," *Gastroenterology*, 138(5):S1-S5 (2010).

Aroniadis et al., "Intestinal Microbiota and the Efficacy of Fecal

(56) References Cited

OTHER PUBLICATIONS

Microbiota Transplantation in Gastrointestinal Disease," Gastroenterology and Hepatology, 10(4): 230-7 (2014).
Aroniadis et al., "Long-Term Follow-up Study of Fecal Microbiota Transplantation (FMT) for Severe or Complicated *Clostridium difficile* Infection (CDI)," *Gastroenterol*, 144(Suppl 1):S185 (2013).
Atarashi et al., "Induction of Colonic Regulatory T Cells by Indigenous *Clostridium* Species," *Science*, 331(6015):337-341, published online Dec. 23, 2010, in U.S. Appl. No. 15/093,679.
Atarashi et al., "$T_{reg}$ induction by a rationally selected mixture of *Clostridia* strains from the human microbiota," *Nature*, 500(7461):232-236 (2013).
Atarashi et al., "WS/PP-064-03 Regulation of colonic regulatory T cells by *Clostridium* species," *International Immunology*, 22(Suppl 1, Part 3), pp. 1-3 (2010).
Atarashi et al., WS-064 Mucosal immunity: homeostasis, 14th ICIC Abstract book, 14th International Congress of Immunology, pp. iii131-iii133 (2010).
Autism, Health Encyclopedia—Diseases and Conditions, The Health Scout Network, pp. 1-5, n.d., Web, Nov. 22, 2005 <www.healthscout.com>.
Autism, Treatment, Prognosis, Healthcommunities.com, Inc., pp. 1-4, n.d., Web. Jan. 28, 2009 <http://www.neurologychannel.com/common/PrintPage.php>.
Autism: Mayo Clinic.com, Mayo Foundation for Medical Education and Research, pp. 1-7, May 31, 2008, Web. Jan. 28, 2009 <http://www.mayoclinic.com/print/autism/DS00348/METHOD=print&DSECTION=all>.
Backhed et al., "Host-bacterial mutualism in the human intestine," *Science*, 307(5717):1915-1920 (2005).
Backhed et al., "Mechanisms underlying the resistance to diet-induced obesity in germ-free mice," *PNAS USA*, 104(3):979-984 (2007).
Backhed et al., "The gut microbiota as an environmental factor that regulates fat storage," *PNAS USA*, 101(44):15718-15723 (2004).
Bakken et al., "Fecal bacteriotherapy for recurrent *Clostridium difficile*infection," Anaerobe, 15(6):285-289 (2009).
Bakken et al., "Treating *Clostridium difficile* Infection with Fecal Microbiota Transplantation," *Clinical Gastroenterology and Hepatology*, 9(12):1044-1049 (2011).
Bartlett et al., "Clinical recognition and diagnosis of *Clostridium difficile* infection," *Clin Infect Dis.*, 46(Suppl 1):S12-S18 (2008)
Bartlett, "Clostridium difficile-associated Enteric Disease," *Curr Infect Dis Rep.*, 4(6):477-483 (2002).
Belkaid et al., "Natural regulatory T cells in infectious disease," *Nature Immunology*, 6(4):353-360 (2005).
Bengmark et al., "Bioecological control of inflammatory bowel disease," *Clinical Nutrition*, 26(2):169-181 (2007).
Bennet et al., "Treatment of ulcerative colitis by implantation of normal colonic flora," *Lancet*, 333(8630):164 (1989).
Benson et al., "Changing epidemiology of Clostridium difficile-associated disease in children," *Infect Control Hosp Epidemiol.*, 28(11):1233-1235 (2007).
Bergey's Manual of Systematic Bacteriology, Second Edition, vol. Three, The Firmicutes, pp. 1-16 (2009).
Blaser et al., "What are the consequences of the disappearing human microbiota?" *Nat. Rev. Microbiol.*, 7(12):887-894 (2009).
Bolte, "Autism and Clostridium tetani," Medical Hypotheses, 51(2):133-144 (1998).
Bolte, "Therapies for Gastrointestinal and Neurological Disorders," U.S. Appl. No. 60/214,813, filed Jun. 28, 2000.
Borody et al., "Fecal microbiota transplantation in gastrointestinal disease: 2015 update and the road ahead," Expert Review of Gastroenterology and Hepatology, 9(11):1379-1391 (2015).
Borody et al., "Anti-MAP Rescues Anti-TNF Failures for Over 4 Years," *Gastroenterol*, 136(5)Suppl 1:A-681 (2009).
Borody et al., "Anti-MAP Therapy for Pediatric Crohn's Disease," *Am J Gastroenterol*, 108(Suppl 1):S516 (2013).
Borody et al., "Anti-MAP Therapy in the Treatment of Active Crohn's Disease," *J Gastroenterol & Hepatol*, 20(Suppl):A2 (2005.

Borody et al., "Anti-mycobacterial therapy in Crohn's disease heals mucosa with longitudinal scars," *Digestive & Liver Disease*, 39(5):438-444 (2007).
Borody et al., "Anti-*Mycobacterium avium* SS *paratuberculosis* (MAP) Therapy and Fistula Closure in Patients with Severe Crohn's Disease," *Am J Gast*, A101:S440 (2006).
Borody et al., "Bacteriotherapy in Chronic Fatigue Syndrome (CFS): A retrospective review," *Am J Gastro*, 107(S1):A1481 (2012).
Borody et al., "Bacteriotherapy Using Fecal Flora: toying with human motions" *J. Clin. Gastroenterol.*, 38(6):475-483 (2004).
Borody et al., "Bowel-flora alteration: a potential cure for inflammatory bowel disease and irritable bowel syndrome?" *Med. J. Aust.*, 150:604 (1989).
Borody et al., "Changes in Crohn's Disease Activity Index and C-Reactive Protein Levels During Anti-MAP Therapy," *AM J Gastro*, 104(S3):A1293 (2009).
Borody et al., "Clostridium difficile Complicating Inflammatory Bowel Disease: Pre- and Post-Treatment Findings," *Gastroenterol*, 134(4)Suppl 1:A-361 (2008).
Borody et al., "Could fecal microbiota transplantation cure all *Clostridium difficile* infections?," *Future Microbiol*, 9:1-3 (2014).
Borody et al., "Entamoeba histolytica: another cause of Crohn's Disease," *AM J Gastro*, 104(S3):A990 (2009).
Borody et al., "Faecal bacteriotherapy (FB) for chronic C. difficile (CD) syndromes," *J Gastroenterol Hepatol*, 18(Suppl.):B8 (Abstract) (2003).
Borody et al., "Fecal bacteriotherapy in the treatment of recurrent *C. difficile* infection," *UpToDate*, pp. 1-6 (2006).
Borody et al., "Fecal Microbiota Transplantation (FMT) in Multiple Sclerosis (MS)," *AM J Gastro*, 106(S2):A942 (2011).
Borody et al., "Fecal microbiota transplantation and emerging applications," *Nat. Rev. Gastroenterol. Hepatol.*, 9(2):88-96 (2011).
Borody et al., "Fecal microbiota transplantation for *Clostridium difficile* infection: A surgeon's perspective" *Seminars in Colon and Rectal Surgery*, 25:163-166 (2014).
Borody et al., "Fecal microbiota transplantation in gastrointestinal diseases—What practicing physicians should know," *Polish Archives of Internal Medicine*, 125(11):852-858 (2015).
Borody et al., "Fecal microbiota transplantation in the treatment of recurrent *Clostridium difficile* infection," *UpToDate*, pp. 1-4, (2015).
Borody et al., "Fecal Microbiota Transplantation in Ulcerative Colitis: Review of 24 Years Experience," *Am J Gastro*, 107(Suppl 1): A1644 (2012).
Borody et al., "Fecal microbiota transplantation: a new standard treatment option for *Clostridium difficile* infection," *Expert Rev Anti Infect Ther.*, 11(5):447-449 (2013).
Borody et al., "Fecal microbiota transplantation: current status and future directions," *Expert Review of Gastroenterology & Hepatology*, 5(6):653-655 (2011).
Borody et al., "Fecal Microbiota Transplantation: Expanding Horizons for *Clostridium difficile* Infections and Beyond," *Antibiotics*, 4:254-266 (2015).
Borody et al., "Fecal Microbiota Transplantation: Indications, Methods, Evidence, and Future Directions," *Curr Gastroenterol Rep*, 15:337-344 (2013).
Borody et al., "Fecal Microbiota Transplantation: Techniques, Applications, and Issues," *Gastroenterol Clin North Am*, 41:781-803 (2012).
Borody et al., "Irritable Bowel Syndrome and Dientamoeba Fragilis," *ASM Sydney National Conference*, pp. 4-5 (2002), in U.S. Appl. No. 15/093,679.
Borody et al., "Is Crohn's Disease Ready for Fecal Microbiota Transplantation?," *J Clin Gastroenterol*, 48(7):582-583 (2014).
Borody et al., "Myoclonus-dystonia affected by GI Microbiota?," *AM J Gastro*, 106(S2):A940 (2011).
Borody et al., "Novel appearance of healing mucosa following anti-*Mycobacterium avium paratuberculosis* therapy for Crohn's disease," *J Gastroenterol Hepatol*, 19(Suppl):A210 (2004).
Borody et al., Reversal of Idiopathic Thrombocytopenic Purpura [ITP] with Fecal Microbiota Transplantation [FMT], *AM J Gastro*, 106(S2):A941 (2011), in U.S. Appl. No. 15/093,679.

(56) References Cited

OTHER PUBLICATIONS

Borody et al., "Reversal of Inflammatory Bowel Disease (IBD) with Recurrent Faecal Microbiota Transplants (FMT)," AM J Gastro, 106(S2):A979 (2011), in U.S. Appl. No. 15/093,679.
Borody et al., "Severe recurrent Crohn's Disease of ileocolonic anastomosis and antimicrobial (anti-mycobacterial therapy)," Gut, 55:1211 (2006).
Borody et al., "The GI Microbiome and its Role in Chronic Fatigue Syndrome: a Summary of Bacteriotherapy," ACNEM Journal, 31(3):3-8 (2012).
Borody et al., "Therapeutic faecal microbiota transplantation: current status and future developments," Curr Opin Gastroenterol, 30:97-105 (2014).
Borody et al., "Treatment of chronic constipation and colitis using human probiotic infusions," Proceedings of Prebiotics and Probiotics and the New Foods Conference, 2-4:228 Abstract (2001).
Borody et al., "Treatment of First-time Clostridium difficile Infection with Fecal Microbiota Transplantation," Poster Presentation, 2015 ACG Annual Scientific Meeting, Honolulu, Hawaii, USA (2015).
Borody et al., "Treatment of Severe Constipation Improves Parkinson's Disease (PD) Symptoms," AM J Gastro, 104(S3):A999 (2009).
Borody et al., "Treatment of Severe Crohn's Disease (CD)—Using Rifabutin-Macrolide-Clofazimine Combination: Results at 30-37 Months," Gastroenterology, 118(4):A1334 Abstract (2000).
Borody et al., Treatment of Severe Crohn's Disease Using Rifabutin-Macrolide-Clofazimine Combination—Results at 38-43 Months, J Gastroenterol & Hepatol, 15(Suppl.):J102 (2000).
Borody et al., "Treatment of Severe Crohn's disease using antimycobacterial triple therapy—approaching a cure?," Digest Liver Dis, 34(1):29-38 (2002).
Borody et al., "Treatment of ulcerative colitis using fecal bacteriotherapy," J. Clin. Gastroenterol., 37(1):42-47 (2003).
Borody, "Bacteriotherapy for Chronic Fatigue Syndrome—A Long Term Follow-Up Study," Proceedings of ACMA Complementary Medicine Sydney, p. 1 (1995).
Borody, "Flora Power"—Fecal Bacteria Cure Chronic C. difficile Diarrhoea, Am J Gastroenterol, 95(11):3028-3029 (2000).
Borody, "Is the Infected Patient too 'Difficile' to Treat?," The Australian Society for Microbiology 2009 Perth, SY03 & SY03.1, p. 27 & 56, (2009).
Borody, "Letter to the Editor—Response to Drs. Famularo et al.," AJG, 96(7):2262-2264 (2001).
Borriello, "Clostridial Disease of the Gut," Clinical Infectious Diseases, The University of Chicago, 20(Suppl 2):S242-S250 (1995).
Bowden et al., "Pseudomembraneous enterocolitis: mechanism of restoring floral homeostasis," Am Surg., 47(4):178-183 (1981).
Brandt et al., "Endoscopic Fecal Microbiota Transplantation: "First-Line" Treatment for Severe Clostridium difficile Infection?" J. Clin. Gastroenterol., 45(8):655-657 (2011).
Brandt et al., "Fecal microbiota transplantation for recurrent Clostridium difficile infection," J Clin Gastroenterol., 45(Suppl):S159-S167 (2011).
Brandt et al., "Long-Term Follow-Up Study of Fecal Microbiota Transplantation (FMT) for Ulcerative Colitis (UC)," Am. J. Gastroenterol., 107(Suppl 1):S657 (2012).
Brandt et al., Safety of Fecal Microbiota Transplantation (FMT) in Immunocompromised (Ic) Patients with Inflammatory Bowel Disease (IBD), Am J Gastroenterol, 108(Suppl 1):S556 (2013).
Browne et al., "Culturing of 'unculturable' human microbiota reveals novel taxa and extensive sporulation," Nature, 533(7604):543-546 (2016).
Bueche et al., "Quantification of Endospore-Forming Firmicutes by Quantitative PCR with the Functional Gene spo0A," Applied and Environmental Microbiology, 79(17):5302-5312 (2013).
Cammorata et al., "Review article: biofile formation by Helicobacter pylori as a target for eradication of resistant infection," Aliment Pharmacol Ther, 36:222-30 (2012).
Campbell et al., "The many faces of Crohn's Disease: Latest concepts in etiology," OJIM, 2(2):107-115 (2012).
Cano et al., "Revival and identification of bacterial spores in 25-40 million year old Dominican Amber Science," Science, 268(5213):1060-1064 (1995).
Cato et al., "Clostridium oroticum comb. nov. amended description," International Journal of Systematic Bacteriology, 17(1):9-13 (1968).
Celik et al., "Factors influencing the stability of freeze-dried stress-resilient and stress-sensitive strains of bifidobacteria," J. Dairy Sci., 96(6):3506-16 (2013).
Center for Disease Control, "Severe Clostridium difficile-associated disease in populations previously at low risk—four states, 2005." Morbidity and Mortality Weekly Report, 54(47):1201-1205 (2005).
Chamberlain et al., "MAP-associated Crohn's Disease, MAP, Koch's postulates, causality and Crohn's Disease," Digestive and Liver Disease, 39:790-794 (2007).
Chamberlin et al., "Primary treatment of Crohn's disease: combined antibiotics taking center stage," Expert Rev. Clin. Immunol., 7(6):751-760 (2011).
Chang et al., "Decreased diversity of the fecal Microbiome in recurrent Clostridium difficile-associated diarrhea," J. Infect. Dis., 197(3):435-438 (2008).
Chen et al., "A mouse model of Clostridium difficile-associated disease," Gastroenterology, 135(6):1984-1992 (2008).
Cherif et al., "Thuricin 7: a novel bacteriocin produced by Bacillus thuringiensis BMG1.7, a new strain isolated from soil," Letters in Applied Microbiology, 32:243-7 (2001).
Chibani-Chennoufi et al., "In Vitro and In Vivo Bacteriolytic Activities of Escherichia coli Phages: Implications for Phage Therapy," Antimicrobial Agents and Chemotherapy, 48(7):2558-2569 (2004).
Choi et al., "Fecal Microbiota Transplantation: Current Applications, Effectiveness, and Future Perspectives," Clin. Endosc., 49:257-265 (2016).
Chopra et al., "Recent epidemiology of Clostridium difficile infection during hematopoietic stem cell transplantation," Clin Transplant., 25(1):E82-E87 (2011).
Chu et al., "Profiling Living Bacteria Informs Preparation of Fecal Microbiota Transplantations," PLOS One, 1-16 (2017).
Citron et al., "In Vitro Activities of CB-183,315, Vancomycin, and Metronidazole against 556 Strains of Clostridium difficile, 445 Other Intestinal Anaerobes, and 56 Enterobacteriaceae Species," Antimicrob Agents Chemother., 56(3):1613-1615 (2012).
Claesson et al., "Comparison of two next-generation sequencing technologies for resolving highly complex microbiota composition using tandem variable 16S rRNA gene regions," Nucleic Acids Research, 38(22):1-13 (2010).
Clancy et al., "Anti-MAP Therapy Induces and Maintains Remission in Severe Crohn's Disease," Ann NY Acad Sci, p. 1 (2005).
Claus et al., "Colonization-induced host-gut microbial metabolic interaction," MBio, 2(2):e00271-00210 (2011).
Claus et al., "Systemic multicompartmental effects of the gut microbiome on mouse metabolic phenotypes," Mol. Syst. Biol., 4(1):219 (2008).
Cohen et al., "Clinical practice guidelines for Clostridium difficile infection in adults: 2010 update by the society for healthcare epidemiology of America (SHEA) and the infectious diseases society of America (IDSA)," Infect Control Hosp Epidemiol., 31(5):431-55 (2010).
Collins et al., "The Phylogeny of the Genus Clostridium: Proposal of Five New Genera and Eleven New Species Combinations," International Journal of Systematic Bacteriology, pp. 812-826 (1994).
U.S. Appl. No. 12/843,409, filed Jul. 26, 2010.
Crohn's Disease, Prevention, Health Guide A-Z, WebMDHealth, pp. 1-2, n.d., Web, Oct. 23, 2005 <http://mywebmd.com/hw/inflammatory.sub.--bowel/uf6012.asp>.
Crowther, "Transport and Storage of Faeces for Bacteriological Examination," Journal of Applied Bacteriology, 34(2):477-483 (1971).
Cutolo et al., "Fecal feedings as a therapy in Staphylococcus enterocolitis," NY State J Med, 59:3831-3833 (1959).
Dale et al., "Molecular interactions between bacterial symbionts and their hosts," Cell, 126(3):453-465 (2006).

(56) References Cited

OTHER PUBLICATIONS

Dan et al., "Comparison of preservation media and freezing conditions for storage of specimens of faeces," J. Med Microbiology, 28:151-154 (1989).
De Giulio et al., "Use of Algiinate and Cryo-Protective Sugars to Improve the Viability of Lactic Acid Bacteria After Freezing and Freeze-Drying," World Journal of Microbiology & Biotechnology, 21:739-746 (2005).
Defang et al., "In vitro and in vivo evaluation of two extended release preparations of combination metformin and glipizide," Drug Develop. & Indust. Pharm., 31:677-685 (2005).
Dendukuri et al., "Probiotic therapy for the prevention and treatment of Clostridium difficile-associated diarrhea: a systematic review," CMAJ, 173(2):167-170 (2005).
Derwent Abstract Accession No. 98-230427/20, WO 98/13068 A, (Kuperman VB) Apr. 2, 1998.
Dethlefsen et al., "An ecological and evolutionary perspective on human-microbe mutualism and disease," Nature, 449(7164):811-818 (2007).
Dewhirst et al., "Phylogeny of the Defind Murine Microbiota: Altered Schaedler Flora," Applied and Environmental Microbiology, 65(8):3287-3292 (1999).
DuPont, "The search for effective treatment of Clostridium difficile infection," N Engl J Med., 364(5):473-475 (2011).
Eckburg et al., "Diversity of the human intestinal microbial flora," Science, 308(5728):1635-1638 (2005).
Eiseman et al., "Fecal enema as an adjunct in the treatment of pseudomembranous enterocolitis," Surgery, 44(5):854-859 (1958).
Eller et al., "Anaerobic Roll Tube Media for Nonselective Enumeration and Isolation and Bacteria in Human Feces," Applied Microbiology, 22(4):522-529 (1971).
Extended European Search Report dated Apr. 3, 2014, in European Patent Application No. 11813951.8.
Extended European Search Report dated Mar. 16, 2018, in European Patent Application No. 17203052.0.
Extended European Search Report dated Nov. 30, 2016, in European Patent Application No. 16193790.9.
Faust et al., "Treatment of recurrent pseudomembranous colitis (RPMC) with stool transplantation (ST): Report of six (6) cases," Can J Gastroenterol., 16:A43 (2002).
Fenton et al., "Pseudomembranous colitis associated with antibiotic therapy—an emerging entity," Can Med Assoc J., 111(10):1110-1111 (1974).
Floch et al., "Probiotics and Dietary Fiber, The Clinical Coming of Age of Intestinal Microecology," J. Clin. Gastroenterology, 27(2):99-100 (1998).
Floch, "Fecal Bacteriotherapy, Fecal Transplant, and the Microbiome," J. Clin. Gastroenterol., 44(8):529-530 (2010).
Flotterod et al., "Refractory Clostridium difficile infection. Untraditional treatment of antibiotic-induced colitis," Tidsskr Nor Laegeforen, 111:1364-1365 (1991).
Frank et al., "Molecular-phylogenetic characterization of microbial community imbalances in human inflammatory bowel diseases," PNAS, 104(34):13780-13785 (2007).
Frantzen et al., "Empirical evaluation of preservation methods for faecal DNA," Molecular Ecology, 7(10):1423-1428 (1998).
Freeman et al., "The changing epidemiology of Clostridium difficile infections," Clin Microbiol. Rev., 23(3):529-549 (2010).
Frese et al., "The evolution of host specialization in the vertebrate gut symbiont Lactobacillus reuteri," PloS Genet., 7(2):e1001314 (2011).
Gaboriau-Routhiau et al., "The Key Role of Segmented Filamentous Bacteria in the Coordinated Maturation of Gut Helper T Cell Responses," Immunity, 31(4):677-689 (2009).
Garborg et al., "Results of faecal donor instillation therapy for recurrent Clostridium difficile-associated diarrhoea," Scand J Infect Dis., 42(11-12):857-61 (2010).
Garey et al., "Meta-analysis to assess risk factors for recurrent Clostridium difficile infection," J. Hosp. Infect., 70(4):298-304 (2008).
Gerding, "Management of Clostridium difficile infection: thinking inside and outside the box," Clin Infect Dis., 51(11):1306-13 (2010).
Geuking et al., "Intestinal Bacterial Colonization Induces Mutualistic Regulatory T Cell Responses," Immunity, 34:794-806 (2011).
Gitlin et al., "*Mycobacterium avium* ss *paratuberculosis*-associated Diseases: Piecing the Crohn's Puzzle Together," J Clin Gastroenterol, 46(8):649-655 (2012).
Gough et al., "Systematic review of intestinal microbiota transplantation (fecal bacteriotherapy) for recurrent Clostridium difficile infection," Clin. Infect. Dis., 53(10):994-1002 (2011).
Grehan et al., "Durable alteration of the colonic microbiota by the administration of donor fecal flora," Journal of Clinical Gastroenterology, 44(8):551-561 (2010).
Guarner et al., "Gut flora in health and disease," Lancet, 361(9356):512-519 (2003).
Gustafsson et al., "The Effect of Faecal Enema on Five Microflora-Associated Characteristics in Patients with Antibiotic-Associated Diarrhoea," Scandinavian Journal of Gastroenterology, 34:580-586 (1999).
Gustafsson et al., "Faecal Short-Chain Fatty Acids in Patients with Antibiotic-Associated Diarrhoea, before and after Faecal Enema Treatment," Scand J Gastroenterol, 33:721-727 (1998).
Hamilton et al., "Change in microbial community composition of in patients with recalcitrant Clostridium difficile colitis treated with fecal bacteriotherapy," International Human Microbiome Congress, Poster and Presentation, Vancouver, ON, Canada, Mar. 9-11, 2011.
Hamilton et al., "High-throughput DNA sequence analysis reveals stable engraftment of gut microbiota following transplantation of gut microbiota following transplantation of previously frozen fecal bateria," Gut Microbes, 4(2):1-11 (2013).
Hamilton et al., "Standardized Frozen Preparation for Transplantation of Fecal Microbiota for Recurrent Clostridium difficile Infection," Article and Supplementary Material, Am. J. Gastroenterol., 107(5):761-767 (2012).
Hayashi et al., "Phylogenetic Analysis of the Human Gut Microbiota Using 16S rDNA Clone Libraries and Strictly Anaerobic Culture-Based Methods," Microbiol. Immunol., 46(8):535-548 (2002).
Hecker et al., "Fecal Microbiota Transplantation by Freeze-Dried Oral Capsules for Recurrent Clostridium difficile Infection," Open Forum Infect Dis, 3(2): 1-2 (2016).
Hellemans et al., "Fecal transplantation for recurrent Clostridium difficile colitis, and underused treatment modality," Acta Gastroenterol Belg., 72(2):269-70 (2009).
Henriksson et al., "Probiotics under the regulatory microscope," Expert Opin. Drug Saf., 4(6):1-9 (2005).
Hensel et al., "Vagal Ascent and Distribution of 125 I-Tetanus Toxin after Injection into the Anterior Wall of the Stomach," Naunyn-Schmiedeberg's Arch. Pharmacol, 276:395-402 (1973).
Honda et al., "Regulation of T Cell Responses by Intestinal Commensal Bacteria," Journal of Intestinal Microbiology, vol. 25, 2nd Edition:104 (2011).
Hongliang et al., "Freeze-dried, Capsulized Fecal Microbiota Transplantation for Relapsing Clostridium difficile Infection," Journal of Clinical Gastroenterology, 43(6):537-538 (2015).
Hooper et al., "How host-microbial interactions shape the nutrient environment of the mammalian intestine," Annu. Rev. Nutr., 22:283-307 (2002).
Hope et al., "Sporadic colorectal cancer-role of the commensal microbiota," FEMS Microbiol. Lett., 244:1-7 (2005).
Hota et al., "Determining Mortality Rates Attributable to Clostridium difficile Infection," Emerg. Infect. Dis., 18(2):305-307 (2012).
Hota et al., "Oral Vancomycin Followed by Fecal Transplant Versus Tapering Oral Vancomycin," U.S. National Institutes of Health, Clinical Study No. NCT01226992, Oct. 20, 2010, last updated Jan. 14, 2013, Web, May 20, 2014, pp. 1-4 <http://clinicaltrials.gov/ct2/show/NCT01226992>.
Hsu et al., "IL-10 Potentiates Differentiation of Human Induced Regulatory T Cells via STAT3 and Foxo1," The Journal of Immunology, 3665-3674 (2015).
Hu et al., "Prospective derivation and validation of a clinical prediction rule for recurrent Clostridium difficile infection," Gastroenterology, 136:1206-1214 (2009).

(56) References Cited

OTHER PUBLICATIONS

Huang et al., "Once-daily propranolol extended-release tablet dosage form: formulation design and in vitro/in vivo investigation," *European J. of Pharm. & Biopharm.*, 58:607-614 (2004).

Huttenhower et al., "Structure, function and diversity of the healthy human microbiome," The Human Microbiome Project Consortium, *Nature*, 486:207-214 (2012).

Immunology in the 21st Century: Defeating Infection, Autoimmunity, Allergy, and Cancer, ICI 2010 Wrap-up Report, 14th International Congress of Immunology, pp. 1 (2010).

Inflammatory Bowel Disease Facts, Disease Prevention and Treatment Strategies, Crohn's Disease and Inflammatory Bowel Disease (IBD), HealingWithNutrition.com, pp. 1-4, n.d., Web, Oct. 23, 2005 <http://www.HealingWithNutrition.com/disease/inflambowels/chrohns.html>.

Information Disclosure Statement filed Nov. 28, 2017, in U.S. Appl. No. 15/487,553.

International Preliminary Examination Report completed Nov. 19, 2002, in International Application No. PCT/AU2001/000907, 19 pgs.

International Preliminary Report on Patentability completed Dec. 12, 2012, in International No. PCT/AU2011/000987, 35 pgs.

International Preliminary Report on Patentability completed Mar. 12, 2015, in International Application No. PCT/AU2013/001362, 29 pgs.

International Preliminary Report on Patentability dated Sep. 10, 2013, in International Application No. PCT/US2012/028484, 10 pgs.

International Search Report and Written Opinion (WO) dated Feb. 2, 2018 in International Application No. PCT/US2017/055618.

International Search Report and Written Opinion (WO) dated Feb. 2, 2018 in International Application No. PCT/US2017/056131.

International Search Report and Written Opinion (WO) dated Feb. 21, 2018 in International Application No. PCT/US2017/056129.

International Search Report and Written Opinion (WO) dated Jan. 17, 2018, in International Application No. PCT/US2017/045092.

International Search Report and Written Opinion (WO) dated Jan. 31, 2018 in International Application PCT/US2017/056126.

International Search Report and Written Opinion dated Aug. 17, 2018, in International Application No. PCT/US2018/034673.

International Search Report and Written Opinion dated Aug. 2, 2018, in International Application No. PCT/US2018/026074.

International Search Report and Written Opinion dated Jul. 30, 2018, in International Application No. PCT/US2018/026080.

International Search Report and Written Opinion dated Aug. 8, 2016, in International Application No. PCT/US2016/032695, 10 pgs.

International Search Report and Written Opinion dated Feb. 5, 2014, in International Application No. PCT/AU2013/001362, 17 pgs.

International Search Report and Written Opinion dated Jan. 5, 2017, in International Application No. PCT/US2016/058938.

International Search Report and Written Opinion dated Jul. 31, 2014, in International Application No. PCT/US2014/027391, 16 pgs.

International Search Report and Written Opinion dated Oct. 28, 2011, in International No. PCT/AU2011/000987, 18 pgs.

International Search Report dated Aug. 10, 2012, in International Application No. PCT/US2012/028484, 7 pgs.

International Search Report dated Jul. 29, 2014, in International Application No. PCT/AU2014/000478, 7 pgs.

International Search Report dated Sep. 22, 2017, in International Application No. PCT/US2017/040591, 12 pgs.

Irrgang et al., "The historical Development of Mutaflor therapy," Ardeypharm GmbH, pp. 1-38 (1988) <http://www.ardeypharm.de/pdfs/en/mutaflor_historical_e.pdf?>.

Irritable Bowel Syndrome (IBS), Health A to Z, InteliHealth, pp. 1-4, n.d., Web, Oct. 23, 2005 <http://www.intelihealth.com>.

Issa et al., "Clostridium difficile and Inflammatory Bowel Disease," *Inflamm Bowel Dis.*, 14(10):1432-1442 (2008).

Issa et al., "Impact of Clostridium difficile on inflammatory bowel disease," *Clin. Gastroenterol. Hepatol.*, 5(3):345-351 (2007).

Itoh et al., "Characterization of clostridia isolated from faeces of limited flora mice and their effect on caecal size when associated with germ-free mice," *Laboratory Animals*, 19:111-118 (1985).

Itoh et al., "Intestinal bacteria antagonistic to Clostridium difficile in mice," *Laboratory Animals*, 21:20-25 (1987).

Ivanov et al., "Specific Microbiota Direct the Differentiation of IL-17-Producing T-Helper Cells in the Mucosa of the Small Intestine," *Cell Host & Microbe*, 4:337-349 (2008).

Jacob et al., "Single Delivery of High-Diversity Fecal Microbiota Preparation by Colonoscopy Is Safe and Effective in Increasing Microbial Diversity in Active Ulcerative Colitis," *Inflamm Bowel Dis.*, 0(0):1-9 (2017).

Janeway et al., "Adaptive Immunity to Infection," *Immunobiology*, 6th Edition, Chapter 10, pp. 414 (2005).

Janeway, Jr. et al., "Autoimmune responses are directed against self antigens," *Immunobiology: The Immune System in Health and Disease*, 5th Edition, pp. 1-4 (2001).

Jarvis et al., "National point prevalence of Clostridium difficile in US health care facility inpatients, 2008," *Am. J. Infect. Control*, 37:263-270 (2009).

Johnson et al., "Interruption of Recurrent Clostridium difficile-Associated Diarrhea Episodes by Serial Therapy with Vancomycin and Rifaximin," *Clin. Infect. Dis.*, 44(6):846-848 (2007).

Johnson et al., "Rifaximin Redux: Treatment of recurrent *Clostridium difficile* infections with Rifaximin immediately post-vancomycin treatment," *Anaerobe*, 15(6):290-291 (2009).

Kageyama et al., "Emendation of genus Collinsella and proposal of Collinsella stercoris sp. nov. and Collinsella intestinalis sp. nov.," International Journal of Systematic and Evolutionary Microbiology, 50:1767-1774 (2000).

Kageyama et al., "Phylogenetic and phenotypic evidence for the transfer of *Eubacterium aerofaciens* to the genus *Collinsella* as *Collinsella aerofaciens* gen. nov., comb. nov.," International Journal of Systematic Bacteriology, 49:557-565 (1999).

Kakihana et al., "Fecal microbiota transplantation for patients with steriod-resistant acute graft-versus-host disease of the gut," *Blood*, 128(16):2083-2088 (2016).

Kamboj et al., "Relapse versus reinfection: surveillance of *Clostridium difficile* infection," *Clin Infect Dis.*, 53(10):1003-1006 (2011).

Kang et al., "Microbiota Transfer Therapy alters gut ecosystem and improves gastrointestinal and autism symptoms: an open-label study," Microbiome, 5:10, 16 pages (2017).

Karas et al., "A review of mortality due to *Clostridium difficile* infection," *J Infect.*, 61(1): 1-8 (2010).

Kassam et al., "Fecal transplant via retention enema for refractory or recurrent *Clostridium difficile* infection," *Arch Intern Med.*, 172(2): 191-193 (2012).

Kelly et al., "Commensal gut bacteria: mechanisms of immune modulation," *TRENDS in Immunology*, 26(6):326-333 (2005).

Kelly et al., "Clostridium difficile—more difficult than ever," *N. Engl. J. Med.*, 359(18):1932-1940 (2008).

Kelly et al., "Clostridium difficile colitis," *N. Engl. J. Med.*, 330(4):257-62 (1994).

Kelly et al., "Fecal Microbiota Transplant for Treatment of *Clostridium difficile* Infection in Immunocompromised Patients," *Am J Gastroenterol*, 109:1065-1071 (2014).

Kelly et al., "Fecal microbiota transplantation for relapsing *Clostridium difficile* infection in 26 patients: methodology and results," *J. Clin. Gastroenterol.*, 46(2):145-149 (2012).

Keynan et al., "The Role of Regulatory T Cells in Chronic and Acute Viral Infections," *Clinical Infectious Diseases*, 46:1046-1052 (2008).

Khanna et al., "A Novel Microbiome Therapeutic Increases Gut Microbial Diversity and Prevents Recurrent *Clostridium difficile* Infection," *The Journal of Infectious Diseases*, 214:173-81 (2016).

Khanna et al., "The epidemiology of community-acquired *Clostridium difficile* infection: a population-based study," *Am J Gastroenterol.*, 107(1):89-95 (2012).

Khanna et al., "The growing incidence and severity of *Clostridium difficile* infection in inpatient and outpatient settings," *Expert Rev Gastroenterol Hepatol.*, 4(4):409-16 (2010).

(56) References Cited

OTHER PUBLICATIONS

Kharidia et al., "The Activity of a Small Lytic Peptide PTP-7 on *Staphylococcus aureus* Biofilms," *J. Microbiol.*, 49(4):663-668 (2011).
Khoruts et al., "Changes in the composition of the human fecal microbiome after bacteriotherapy for recurrent *Clostridium difficile*-associated diarrhea," *J. Clin Gastroenterol.*, 44(5):354-360 (2010).
Khoruts et al., "Therapeutic transplantation of the distal gut microbiota," *Mucosal Immunol.*, 4(1):4-7 (2011).
Kim et al., "Effect of Rifampin on the Plasma Concentration and the Clinical Effect of Haloperidol Concomitantly Administered to Schizophrenic Patients," Journal of Clinical Psycopharmacology, 16(3):247-252 (1996).
Kim et al., "In Vitro Culture Conditions for Maintaining a Complex Population of Human Gastrointestinal Tract Microbiota," Journal of Biomedicine and Biotechnology, 2011(Article ID 838040):1-10 (2011) <http://www.hindawi.com/journals/bmri/2011/838040/>.
Klaenhammer, "Bacteriocins of lactic acid bacteria," Biochimie, 70:337-49 (1988).
Kleiman et al., "Comparison of two coprological methods for the veterinary diagnosis of fasciolosis," *Arquivo Brasileiro de Medicina Veterinária e Zootécnica*, 55(2):181-185 (2005).
Kobashi et al., "Metabolism of Sennosides by Human Intestinal Bacteria," Journal of Medicinal Plant Research, 40(3):225-236 (1980).
Koch, "What size should a bacterium be? A question of scale," Annu. Rev. Microbiol., 50:317-48 (1996).
Krogius-Kurikka et al., "Sequence analysis of percent G+C fraction libraries of human faecal bacterial DNA reveals a high number of *Antinobacteria*," *BMC Microbiology*, 9(68):1-13 (2009).
Kuijper et al. "Update of *Clostridium difficile* Infection due to PCR Ribotype 027 in Europe, 2008," *Euro. Surveill.*, 13(31):Article 5 (2008).
Kuksal et al., "Formulation and In Vitro, In Vivo Evaluation of Extended-release Matrix Tablet of Zidovudine: Influence of Combination of Hydrophilic and Hydrophobic Matrix Formers," *AAPS Pharm.*, 7(1):E1-E9 (2006).
Kunde et al., "Safety, Tolerability, and Clinical Response After Fecal Transplantation in Children and Young Adults With Ulcerative Colitis," *JPNG*, 56(6):597-601 (2013).
Kyne et al., "Association between antibody response to toxin A and protection against recurrent Clostridium difficile diarrhea," *Lancet*, 357(9251):189-93 (2001).
Kyne et al., "Asymptomatic carriage of Clostridium difficile and serum levels of IgG antibody against toxin A," *N Engl J Med.*, 342(6):390-397 (2000).
Kyne et al., "Factors associated with prolonged symptoms and severe disease due to Clostridium difficile," *Age and Ageing*, 28(2):107-13 (1999).
Kysela et al., "Serial analysis of V6 ribosomal sequence tags (SARST-V6): a method for efficient, high-throughput analysis of microbial community composition," *Environmental Microbiology*, 7(3):356-364 (2005).
Labbé et al., "*Clostridium difficile* infections in a Canadian tertiary care hospital before and during a regional epidemic associated with the BI/NAP1/027 strain," *Antimicrob Agents Chemother.*, 52(9):3180-7 (2008).
Lamontagne et al., "Impact of emergency colectomy on survival of patients with fulminant Clostridium difficile colitis during an epidemic caused by a hypervirulent strain," *Ann. Surg.*, 245(2):267-272 (2007).
Larsen et al., "Gut Microbiota in Human Adults with Type 2 Diabetes Differs from Non-Diabetic Adults," PLoS One, 5(2): e9085-e9095 (2010).
Lau et al., "Bacteraemia caused by *Anaerotruncus colihominis* and emended description of the species," *J Clin Pathol*, 59:748-752 (2006).
Lawson et al., "*Anaerotruncus colihominis* gen. nov., sp. nov., from human faeces," *International Journal of Systematic and Evolutionary Microbiology*, 54:413-417 (2004).

Lawson et al., "Anaerotruncus," *Bergey's Manual of Systematics of Archae and Bacteria*, pp. 1-4 (2009).
Lee et al., "The outcome and long-term follow-up of 94 patients with recurrent and refractory *Clostridium difficile* infection using single to multiple fecal microbiota transplantation vie retention enema," *European Journal Clinical Microbiology Infect Dis.*, 33:1425-1428 (2014).
Lee, "A Prospective Randomized Multi-Centre Trial of Fresh vs. Frozen-and-Thawed Human Biotherapy (Fecal Transplant) for Recurrent *Clostridium difficile* Infection," U.S. National Institutes of Health, Clinical Study No. NCT01398969, pp. 1-4, last updated Feb. 27, 2014, Web, May 20, 2014 <http://clinicaltrials.gov/ct2/show/NCT01398969>.
Leis et al., "Fecal microbiota transplantation: A 'How-To' guide for nurses," *Collegian*, 22:445-451 (2015).
Leslie et al., "Trehalose and Sucrose Protect Both Membranes and Proteins in Intact Bacteria during Drying," Applied and Environmental Microbiology, 61:3592-3597 (1995).
Lewis et al., "Stool form scale as a useful guide to intestinal transit time," *Scand. J. Gastroenterol.*, 32(9):920-924 (1997).
Ley et al., "Ecological and evolutionary forces shaping microbial diversity in the human intestine," *Cell*, 124:837-848 (2006).
Ley et al., "Evolution of mammals and their gut microbes," *Science*, 320(5883):1647-1651 (2008).
Ley et al., "Microbial ecology: human gut microbes associated with obesity," *Nature*, 444(7122):1022-3 (2006).
Ley et al., "Worlds within worlds: evolution of the vertebrate gut microbiota," *Nat. Rev. Microbiol.*, 6(10):776-788 (2008).
Lin et al., "Twelve Week Storage Trial of Microbial Viability in Lyophilized and Frozen Fecal Microbiota Preparations," Poster Presentation—Digestive Disease Week 2015, Washington, D.C. USA.
Longstreth, "Irritable bowel syndrome: A multibillion-dollar problem," Gastroenterology, 109(6):2029-2031 (1995).
Loo et al., "A predominantly clonal multiinstitutional outbreak of Clostridium difficile-associated diarrhea with high morbidity and mortality," *N Engl J Med*, 353(23):2442-9 (2005).
Loo et al., "Host and pathogen factors for *Clostridium difficile* infection and colonization," *N Engl J Med*, 365(18):1693-703 (2011).
Louie et al., "Fidaxomicin versus vancomycin for *Clostridium difficile* infection," *N. Engl. J. Med.*, 364(5):422-431 (2011).
Louie et al., "Home-based fecal flora infusion to arrest multiply-recurrent *C. difficile* infection," ICAAC/IDSA Conference, Abstract #K-4201 (2008).
Louis et al., "Diversity, metabolism and microbial ecology of butyrate-producing bacteria from the human large intestine," *FEMS Microbiology Letters*, 294:1-8 (2009).
Lu, "Taboo transplant: How new poo defeats superbugs," Science News, 1:90-91 (2011) (with English translation).
Ludwig et al., "Taxonomic outline of the phylum Firmicutes," Bergey's Manual of Systematic Bacteriology, 3:15-17 (2009).
Lund-Tonnesen et al., "Clostridium difficile-associated diarrhea treated with homologous faeces," *Tidsskr nor Lageforen*, 118:1027-1030 (1998) (with English translation).
MacConnachie et al., "Faecal transplant for recurrent Clostridium difficile-associated diarrhoea: a UK case series," *QJM*, 102(11):781-784 (2009).
MacDonald et al., "Formation of Ursodeoxycholic Acid from Chenodeoxycholic Acid by a 7β-Hydroxysteroid Dehydrogenase-Elaborating *Eubacterium aerofaciens* Strain Cocultured with 7α-Hydroxysteroid Dehydrogenase-Elaborating Organisms," Applied and Environmental Microbiology, 44(5):1187-1195 (1982).
Macpherson et al., "Induction of Protective IgA by Intestinal Dendritic Cells Carrying Commensal Bacteria," *Science*, 303:1662-1665 (2004).
Madsen, "The use of probiotics in gastrointestinal disease," Can J Gastroenterol, 15(12):817-22 (2001).
Maizels et al., "Regulatory T cells in Infection," *Advances in Immunology*, Chapter 3, 112:73-136 (2011).
Marchesi et al., "The normal intestinal microbiota," *Curr. Opin. Infect. Dis.*, 20(5):508-513 (2007).

(56) References Cited

OTHER PUBLICATIONS

Martin, "Development and Delivery of a Treatment for Clostridiumdifficile," *Bacteriotherapy*, pp. 1-2, n.d., Web, Feb. 10, 2012 <www.bacteriotherapy.org>.
Martin-Dejardin et al., "A way to follow the viability of encapsulated *Bifidobacterium bifidum* subjected to a freeze-drying process in order to target the colon: Interest of flow cytometry," European Journal of Pharmaceutical Sciences, 49:166-74 (2013).
Maslowski et al., "Diet, gut microbiota and immune responses," *Nat Immunol.*, 12(1):5-9 (2011).
McDonald et al., "An Epidemic, Toxin Gene-Variant Strain of *Clostridium difficile*," *N Engl J Med.*, 353(23):2433-41 (2005).
McDonald et al., "*Clostridium difficile* Infection in Patients Discharged from US Short-stay Hospitals, 1996-2003" *Emerg. Infect. Dis*, 12(3):409-415 (2006).
McFarland et al., "Breaking the Cycle: Treatment Strategies for 163 Cases of Recurrent Clostridium difficile Disease," *Am. J. Gastroenterol.*, 97(7):1769-1775 (2002).
McFarland et al., "Implications of the changing face of Clostridium difficile disease for health care practitioners," *Am J Infect Control.*, 35(4):237-253 (2007).
McFarland et al., "Meta-Analysis of Probiotics for the Prevention of Antibiotic Associated Diarrhea and the Treatment of Clostridium difficile Disease," *Am J Gastroenterol.*, 101(4):812-22 (2006).
McFarland et al., "Nosocomial Acquisition of *Clostridium difficile* Infection," *N Engl J Med.*, 320(4):204-210 (1989).
McFarland et al., "Recurrent Clostridium Difficile Disease: Epidemiology and Clinical Characteristics," *Infect Control Hosp Epidemiol.*, 20(1):43-50 (1999).
McFarland et al., "Renewed interest in a difficult disease: *Clostridium difficile* infections—epidemiology and current treatment strategies," *Curr Opin Gastroenterol.*, 25(1):24-35 (2008), in U.S. Appl. No. 15/093,679.
Miller et al., "Health care-associated *Clostridium difficile* infection in Canada: patient age and infecting strain type are highly predictive of severe outcome and mortality," Clin Infect Dis., 50(2):194-201 (2010), in U.S. Appl. No. 15/093,679.
Miller et al., "Long-term follow-up of patients with fulminant Clostridium difficile colitis," *J. Gastrointest. Surg.*, 13(5):956-959 (2009), in U.S. Appl. No. 15/093,679.
Miller et al., "Morbidity, mortality, and healthcare burden of nosocomial Clostridium difficile-associated diarrhea in Canadian hospitals," *Infect Control Hosp Epidemiol.*, 23(3):137-40 (2002), in U.S. Appl. No. 15/093,679.
Miller, "The fascination with probiotics for *Clostridium difficile* infection: lack of evidence for prophylactic or therapeutic efficacy," *Anaerobe*, 15(6):281-284 (2009), in U.S. Appl. No. 15/093,679.
Moayyedi et al., "Fecal Microbiota Transplantation Induces Remission in Patients With Active Ulcerative Colitis in a Randomized Controlled Trial," Gastroenterology, 149(1):102-9 (2015), in U.S. Appl. No. 15/093,679.
Molecular Studies in Autism, 2004 Funding Cycle, Cure Autism Now, Cure Autism Now Foundation, pp. 1-7 (2005) <www.cureautismnow.org>, in U.S. Appl. No. 15/093,679.
Momose et al., "16S rRNA gene sequence-based analysis of clostridia related to conversion of germfree mice to the normal state," *Journal of Applied Microbiology*, 107:2088-2097 (2009).
Morris et al., "Clostridium difficile Colitis: An Increasingly Aggressive Iatrogenic Disease?" *Arch Surg.*, 137(10):1096-1100 (2002).
Mucosal immunity: homeostasis (WS-064): Chairpersons: Toshiaki Ohteki, Makoto Iwata, *International Immunology*, 22:Suppl 1 Pt. 3, 1-9 (2010).
Mullard, "Microbiology: The Inside Story," *Nature*, 453:578-580 (2008).
Murai et al., "Interleukin 10 acts on regulatory T cells to maintain expression of the transcription factor Foxp3 and suppressive function in mice with colitis," *Nat Immunol.*, pp. 1-20 (2009).
Mutaflor, "Brief Summary of Therapeutic Principles," Ardeypharm GmbH 0796 D-58313 Herdecke Germany, 6 pgs (2006).
Mutaflor, "For Functional and Inflammatory Bowel Diseases for Extraintestinal Manifestations for Activation of the Body's In-Built Defences," Ardeypharm GmbH 0796, D-58313 Herdecke Germany, 8 pgs (2006).
Mutaflor, "Safety of Therapy," Ardeypharm GmbH 0796, D-58313 Herdecke Germany, 4 pgs (1988).
Muto et al., "A Large Outbreak of Clostridium difficile-Associated Disease with an Unexpected Proportion of Deaths and Colectomies at a Teaching Hospital Following Increased Fluoroquinolone Use," *Infect Control Hosp Epidemiol.*, 26(3):273-80 (2005).
Nieuwdorp et al., ["Treatment of recurrent Clostridium difficile-associated diarrhoea with a suspension of donor faeces"], *Ned Tijdschr Geneeskd*, 152(35):1927-32 (2008) (English absract).
Niu et al., "Prevalence and Impact of Bacteriophages on the Presence of *Escherichia coli* O157:H7 in Feedlot Cattle and Their Environment," Applied and Environmental Microbiology, 75(5):1271-8 (2009).
O'Hara et al., "The gut flora as a forgotten organ," *EMBO Rep.*, 7(7):688-693 (2006).
O'Brien et al., "The emerging infectious challenge of clostridium difficile-associated disease in Massachusetts hospitals: clinical and economic consequences," Infect Control Hosp Epidemiol., 28(11):1219-27 (2007).
O'Connor et al., "*Clostridium difficile* Infection Caused by the Epidemic BI/NAP1/027 Strain," *Gastroenterology*, 136(6):1913-1924 (2009).
Office Action dated Sep. 18, 2015, in European Patent Application No. 11 728 077.6.
O'Garra et al., "IL-10—producing and naturally occuring CD4+ Tregs: limiting collateral damage," *The Journal of Clinical Investigation*, 114:1372-1378 (2004).
Okada et al., "Effects of Fecal Microorganisms and Their Chloroform-Resistant Variants Derived from Mice, Rats, and Humans on Immunological and Physiological Characteristics of the Intestines of Ex-germfree Mice," *Infection and Immunity*, 62(12):5442-5446 (1994).
Olson et al., "The Gut Microbiota Mediates the Anti-Seizure Effects of the Ketogenic Diet," Cell, 173:1728-1741 (2018) <https://linkinghub.elsevier.com/retrieve/pii/S0092867418305208>.
Ott et al., "Efficacy of Sterile Fecal Filtrate Transfer for Treating Patients With *Clostridium difficile* Infection," Gastroenterology, 152(4):799-811 (2017).
Paramsothy et al., "Gastroenterologist perceptions of faecal microbiota transplantation," *World J Gastroenterol*, 21(38): 10907-10914 (2015).
Paramsothy et al., "Multidonor intensive faecal microbiota transplantation for active ulcerative colitis: a randomised placebo-controlled trial," The Lancet, published online, 11 pages (2017).
Patterson et al., "Special organism isolation: attempting to bridge the gap," *Infect Control Hosp Epidemiol.*, 15(5):335-338 (1994).
Pearce et al., "Modification of the colonic microflora using probiotics: The way forward?," *Gut*, 41(Suppl 3):A63 (1997).
Pearce et al., "The use of probiotic therapy as a novel approach to the management of irritable bowel syndrome: a preliminary study," *J Gastroenterol & Hepatol*, 12(Suppl):A129 (1997).
Pépin et al., "Clostridium difficile-associated diarrhea in a region of Quebec from 1991 to 2003: a changing pattern of disease severity," *CMAJ*, 171(5):466-472 (2004).
Pépin et al., "Emergence of Fluoroquinolones as the Predominant Risk Factor for Clostridium difficile-Associated Diarrhea: A Cohort Study During an Epidemic in Quebec," *Clin Infect Dis.*, 41(9):1254-1260 (2005).
Pépin et al., "Management and Outcomes of a First Recurrence of Clostridium difficile-Associated Disease in Quebec, Canada," *Clin. Infect. Dis.*, 42:758-764 (2006).
Persky et al., "Treatment of recurrent Clostridium difficile-associated diarrhea by administration of donated stool directly through a colonoscope," *Am J Gastroenterol.*, 95(11):3283-3285 (2000).
Petrof et al., "Stool substitute transplant therapy for the eradication of *Clostridium difficile* infection: 'RePOOPulating' the gut," *Microbiome*, 1:3 (2013).
Petrof, "Harnessing the healthy gut microbiota to cure patients with recurrent *C. difficile* infection," U.S. National Institutes of Health,

(56) References Cited

OTHER PUBLICATIONS

Clinical Study No. NCT01372943, pp. 1-2, last updated Nov. 6, 2013, Web, May 22, 2014 <http://clinicaltrials.gov/ct2/show/NCT01372943>.
Pillai et al., "Probiotics for treatment of Clostridium difficile-associated colitis in adults (Review)," *Cochrane Database Syst Rev.*, (1):CD004611 (2008).
Porter, "Coating of pharmaceutical dosage forms," in D.B. Troy (Ed.), Remington: The Science and Practice of Pharmacy, Chapter 46, pp. 929-938 (2005).
Poster 064-03 presented at the 14th International Congress of Immunology, Aug. 22-27, 2010, in Kyoto (Atarashi et al., Regulation of colonic regulatory T cells by *Clostridium* species).
Prakash et al., "Colon-targeted delivery of live bacterial cell biotherapeutics including microencapsulated live bacterial cells," *Biologics: Targets & Therapy*, 2(3):355-378 (2008).
Prevention of Sudden Infant Death Syndrome, Healthtouch.com, *Thomson MICROMEDEX*, pp. 1-4, n.d., Web, Nov. 23, 2005.
Qiu et al., "*Faecalibacterium prausnitzii* upregulates regulatory T cells and anti-inflammatory cytokines in treating TNBS-induced colitis," *Journal of Crohn's and Colitis*, 7:e558-e568 (2013).
Rabeneck et al., "Bleeding and perforation after outpatient colonoscopy and their risk factors in usual clinical practice," *Gastroenterology*, 135(6):1899-1906 (2008).
Rager et al., "Evaluation of rumen transfaunation after surgical correction of left-sided displacement of the abomasum in cows," *J. Am. Vet. Med. Assoc.*, 225(6):915-920 (2004).
Ramesh et al., "Prevention of Clostridium difficile-induced ileocecitis with Bacteriophage," *Anaerobe*, 5:69-78 (1999).
Rao et al., "Evaluation of gastrointestinal transit in clinical practice: position paper of the American and European Neurogastroenterology and Motility Societies," *Neurogastroenterol. Motil.*, 23(1):8-23 (2011).
Rautava, "Potential uses of probiotics in the neonate," Seminars in Fetal & Neonatal Medicine, 12:45-53 (2007).
Rea et al., "Gut solutions to a gut problem: bacteriocins, probiotics and bacteriophage for control of *Clostridium difficile* infection," Journal of Medical Microbiology, 62:1369-1378 (2013).
Redelings et al., "Increase in Clostridium difficile-related mortality rates, United States, 1999-2004," *Emerg Infect Dis.*, 13(9):1417-1419 (2007).
Response to Office Action filed Feb. 25, 2014, in European Patent Application No. 11 728 077.6.
Response to Office Action filed Jan. 28, 2015, in European Patent Application No. 11 728 077.6.
Response to Office Action filed Nov. 18, 2015, in European Patent Application No. 11 728 077.6.
Rex et al., "American College of Gastroenterology guidelines for colorectal cancer screening 2008," *Am. J. Gastroenterol.*, 104(3):739-750 (2009).
Ricciardi et al., "Increasing prevalence and severity of Clostridium difficile colitis in hospitalized patients in the United States," *Arch Surg.*, 142(7):624-631 (2007).
Roberts, Generation and Development Microbial Drug Products, CSO Vedanta Biosciences, 1st Microbiome Drug Development Summit, pp. 1-17 (2016).
Rodemann et al., "Incidence of *Clostridium difficile* infection in inflammatory bowel disease," *Clin Gastroenterol Hepatol.*, 5(3):339-344 (2007).
Rohlke et al., "Fecal flora reconstitution for recurrent *Clostridium difficile* infection: results and methodology," *J Clin Gastroenterol.*, 44(8):567-570 (2010).
Rolfe et al., "Bacterial interference between *Clostridium difficile* and normal fecal flora," *J Infect Dis.*, 143(3):470-475 (1981).
Rossen et al., "Findings From a Randomized Controlled Trial of Fecal Transplantation for Patients with Ulcerative Colitis," Gastroenterology, 149(1):110-8 (2015).
Round et al., "Inducible Foxp3+ regulatory T-cell development by a commensal bacterium of the intestinal microbiota," *PNAS*, 107(27):12204-12209 (2010).

Round et al., "The gut microbiota shapes intestinal immune responses during health and disease," *Nat. Rev. Immunol.*, 9(5):313-323 (2009).
Rupnik et al., "*Clostridium difficile* infection: new developments in epidemiology and pathogenesis," *Nat. Rev. Microbiol.*, 7(7):526-536 (2009).
Russell et al., "Fecal bacteriotherapy for relapsing *Clostridium difficile* infection in a child: a proposed treatment protocol," *Pediatrics*, 126(1):e239-42 (2010).
Sambol et al., "Colonization for the prevention of Clostridium difficile disease in hamsters," *J. Infect. Dis.*, 186(12):1781-1789 (2002).
Sanchez et al., "The Role of Natural Regulatory T cells in Infection," *Immunol Res.*, 49(0):124-134 (2011).
Sandler et al., "Possible Gut-Brain Interaction Contributing to Delayed Onset Autism Symptomatology," Fourth Int. Symp. Brain-Gut Interactions, Blackwell Science Ltd., 10(4):33 (1998).
Sandler et al., "Short-Term Benefit From Oral Vancomycin Treatment of Regressive-Onset Autism," Journal of Child Neurology, 15(7):429-435 (2000).
Sartor, "Therapeutic correction of bacterial dysbiosis discovered by molecular techniques," *PNAS*, 105(43):16413-16414 (2008).
Schiller, "Review article, the therapy of constipation," Ailment Pharmacol. Ther., 15:749-763 (2001).
Scholss, "Introducing mothur: Open-Source, Platform-Independent, Community-Supported Software for Describing and Comparing Microbial Communities," *Appl. Environ. Microbiol.*, 75(23):7537-7541 (2009).
Schwan et al., "Relapsing Clostridium Difficile Enterocolitis Cured by Rectal Infusion of Homologous Faeces," *The Lancet*, 322(8354):845 (1983).
Schwan et al., "Relapsing Clostridium difficile Enterocolitis Cured by Rectal Infusion of Normal Faeces," *Scand. J. Infect. Dis.*, 16(2):211-215 (1984).
Seeff et al., "How many endoscopies are performed for colorectal cancer screening? Results from CDC's survey of endoscopic capacity," *Gastroenterology*, 127:1670-1677 (2004).
Sekirov et al., "Gut microbiota in health and disease," *Physiol. Rev.*, 90(3):859-904 (2010).
Sell et al., "Bacteriophage and Bacteriocin Typing Scheme for *Clostridium difficile*," Journal of Clinical Microbiology, 17(6):1148-1152 (1983).
Setlow, "I Will Survive: Protecting and Repairing Spore DNA," Journal of Bacteriology, 174(9):2737-2741 (1992).
Setlow, "The bacterial spore: nature's survival package," Culture, 26(2):1-4 (2005).
Sghir et al., "Quantification of Bacterial Groups within Human Fecal Flora by Oligonucleotide Prode Hybridization," *Applied and Environmental Microbiology*, 66(5):2263-2266 (2000).
Shim et al., "Primary symptomless colonisation by Clostridium difficile and decreased risk of subsequent diarrhea," *The Lancet*, 351(9103):633-666 (1998).
Silverman et al., "Success of self-administered home fecal transplantation for chronic *Clostridium difficile* infection," *Clin. Gastroenterol. Hepatol.*, 8(5):471-473 (2010).
Simor et al., "Clostridium difficile in long-term-care facilities for the elderly," *Infect Control Hosp Epidemiol.*, 23(11):696-703 (2002).
Singh et al., "Do NSAIDs, antibiotics, infections, or stress trigger flares in IBD?" *Am J Gastroenterol.*, 104(5): 1298-1313 (2009).
Sleator, "The human superorganism—of microbes and men," *Med. Hypotheses*, 74(2):214-215 (2010).
Smits et al., "Therapeutic potential of fecal microbiota transplantation," Gastroenterology, 145:946-953 (2013).
Sokol et al., *Faecalibacterium prausnitzii* is an anti-inflammatory commensal bacterium identified by gut microbiota analysis of Crohn disease patients, *Proceedings of the National Academy of Sciences*, 105(43):16731-16736 (2008).
Sokol et al., "Low Counts of *Faecalibacterium prausnitzii* in Colitis Microbiota," *Inflamm. Bowel Dis.*, pp. 1-7 (2009).
Sullivan et al., "Effect of supplement with lactic-acid producing bacteria on fatigue and physical activity in patients with chronic fatigue syndrome," Nutritional Journal, 8(4):1-6 (2009).

(56) References Cited

OTHER PUBLICATIONS

Sunil et al., "Design and evaluation of lornoxicam bilayered tablets for biphasic release," Brazilian Journal of Pharmaceutical Sciences, 48(4):609-19 (2012).
Surawicz et al., "Treatment of refractory and recurrent *Clostridium difficile* infection," *Nat. Rev. Gastroenterol. Hepatol.*, 8(6):330-339 (2011).
Surawicz, "Reining in Recurrent *Clostridium difficile* Infection—Who's at Risk?," *Gastroenterology*, 136:1152-1154 (2009).
Sutherland et al., "Lyophilized Clostridium perfringens 3 alpha- and Clostridium bifermentans 7 alpha-hydroxysteroid dehydrogenases: two new stable enzyme preparations for routine bile acid analysis," Biochim Biophys Acta, 962(1):116-121 (1988).
Takaishi et al., "Imbalance in intestinal microflora constitution could be involved the pathogenesis of inflammatory bowel disease," *J. Med. Microbiol.*, 298:463-472 (2008).
Takeda et al., "Serum Haloperidol Levels of Schizophrenics Receiving Treatment for Tuberculosis," Clinical Neuropharmacology, 9(4):386-397 (1986).
Tannock et al., "A new macrocyclic antibiotic, fidaxomicin (OPT-80), causes less alteration to the bowel microbiota of *Clostridium difficile*-infected patients than does vancomycin," *Microbiology*, 156(11):3354-3359 (2010).
Tanoue et al., "Immune response to gut microbiota-commensals and pathogens," Gut Microbes, 1(4):224-233 (2010).
Taras et al., "Reclassification of *Eubacterium formicigenerans* Holdeman and Moore 1974 as *Dorea formicigenerans* gen. nov., comb. nov., and description of *Dorea longicatena* sp. nov., isolated from human faeces," *International Journal of Systematic and Evolutionary Microbiology*, 52:423-428 (2002).
Teasley et al., "Prospective randomised trial of metronidazole versus vancomycin for Clostridium-difficile-associated diarrhoea and colitis," *The Lancet*, 2(8358):1043-1046 (1983).
Tilg et al., "Gut microbiome, obesity, and metabolic dysfunction," *J. Clin. Invest.*, 121(6):2126-2132 (2011).
Tvede et al., "Bacteriotherapy for chronic relapsing Clostridium difficile diarrhea in six patients," *The Lancet*, 1:1156-1160 (1989).
Van Andel et al., "Interleukin-12 Has a Role in Mediating Resistance of Murine Strains to Tyzzer's Disease," *Infect. Immun.*, 66(10):4942-4946 (1998).
Van der Waaij et al., "Direct Flow Cytometry of *Anaerobic* Bacteria in Human Feces," *Cytometry*, 16:270-279 (1994).
Van Immerseel et al., "Butyric acid-producing *anaerobic* bacteria as a novel probiotic treatment approach for inflammatory bowel disease," *Journal of Medical Microbiology*, 59:141-143 (2010).
Van Nood et al., "Struggling with Recurrent *Clostridium difficile* Infections: Is Donor Faeces the Solution?," *Euro Surveill.*, 14(34):1-6 (2009).
Van Nood, "Duodenal infusion of donor feces for recurrent Clostridium difficile," *New England Journal of Medicine*, 368(5):407-415 (2013).
Vaughn et al., "Novel treatment options for ulcerative colitis," *Future Science*, 1-20 (2013).
Veldhuyzen van Zanten et al., "Drug Treatment of Functional Dyspepsia: A Systematic Analysis of Trial Methodology with Recommendations for Design of Future Trials," *Am. J. Gastroenterol.*, 91(4):660-673 (1996).
Veldhuyzen van Zanten et al., "Validation of a 7-point Global Overall Symptom scale to measure the severity of dyspepsia symptoms in clinical trials," *Ailment Pharmacol. Ther.*, 23(4):521-529 (2006).
Venugopal et al., "Fidaxomicin: A Novel Macrocyclic Antibiotic Approved for Treatment of *Clostridium difficile* Infection," *Clin Infect Dis*, 54(4):568-74 (2012).
Vrieze et al., "The environment within: how gut microbiota may influence metabolism and body composition," *Diabetologia*, 53(4):606-613 (2010).
Vulevic et al., "Modulation of the fecal microflora profile and immune function by a novel trans-galactooligosaccharide mixture (B-GOS) in healthy elderly volunteers," Am J Clin Nutr, 88:1438-46 (2008).
Wachsmann et al., "Characterization of an Orotic Acid Fermenting Bacterium, *Zymobacterium oroticum*, nov. gen., nov. spec.," *Journal of Bacteriology*, 68(4):400-404 (1954).
Walter et al., "Host-microbial symbiosis in the vertebrate gastrointestinal tract and the Lactobacillus reuteri paradigm," *PNAS USA*, 108(Suppl 1):4645-4652 (2011).
Warny et al., "Toxin production by an emerging strain of Clostridium difficile associated with outbreaks of severe disease in North America and Europe," *Lancet*, 366(9491):1079-84 (2005).
Warren et al., "*Clostridium aldenense* sp. nov. and *Clostridium citroniae* sp. nov. Isolated from Human Clinical Infections," *Journal of Clinical Microbiology*, 44(7):2416-2422 (2006).
Wasfy et al., "Comparison of Preservation Media for Storage of Stool Samples," Journal of Clinical Microbiology, 33(8):2176-2178 (1995).
Weingarden et al., "Dynamic changes in short- and long-term bacterial composition following fecal microbiota transplantation for recurrent *Clostridium difficile* infection," Microbiome, 3(10), 8 pages (2015).
Weissman et al., "Stool Transplants: Ready for Prime Time?," Current Gastroenterology Reports, 14:313-316 (2012).
Wells et al., "Clostridia: Sporeforming Anaerobic Bacilli," *Medical Microbiology—NCBI Bookshelf*, 4th Edition, Chapter 18, pp. 1-20 (1996) <https://www.ncbi.nlm.nih.gov/books/NBK8219/?report=printable>.
Wenisch et al., "Comparison of Vancomycin, Teicoplanin, Metronidazole, and Fusidic Acid for the Treatment of Clostridium difficile-Associated Diarrhea," *Clin Infect Dis.*, 22(5):813-818 (1996).
Wettstein et al., "Fecal Bacteriotherapy—An effective Treatment for Relapsing Symptomatic *Clostridium difficile* Infection," Abstract, 15th United European Gastroenterology Week (UEGW) Poster presentations, United European Gastroenterology Federation, France, A303 (2007).
Wettstein et al., "Skewered diverticulum: another cause of abdominal pain," *Internal Med J*, 31(8):495-496 (2001).
Wikoff et al., "Metabolomics analysis reveals large effects of gut microflora on mammalian blood metabolites," *PNAS*, 106(10):3698-3703 (2009).
Wilson et al., "Human Colonic Biota Studied by Ribosomal DNA Sequence Analysis," *Appl. Environ. Microbiol.*, 62(7):2273-2278 (1996).
Yoon et al., "Treatment of Refractory/Recurrent C. difficile-associated Disease by Donated Stool Transplanted Via Colonoscopy: A Case Series of 12 patients," *J Clin Gastroenterol.*, 44(8):562-566 (2010).
You et al., "Successful treatment of fulminant *Clostridium difficile* infection with fecal bacteriotherapy," *Ann. Intern. Med.*, 148(8):632-633 (2008).
Youngster et al., "Oral, Capsulized, Frozen Microbiota Transplantation for Relapsing *Clostridium difficile* Infection," *American Medical Association*, 312 (174) 1772-1778 (2014).
Yue et al., "Similarity Measure Based on Species Proportions," *Commun. Stat. Theor. Methods*, 34(11):2123-2131 (2005).
Zar et al., "A Comparison of Vancomycin and Metronidazole for the Treatment of Clostridium difficile-Associated Diarrhea, Stratified by Disease Severity," *Clin Infect Dis.*, 45(3):302-307 (2007).
Zhou et al., "Total fecal microbiota transplantation alleviates high-fat diet-induced steatohepatitis in mice via beneficial regulation of gut microbiota," *Scientific Reports (Nature)*, 7(1529):1-11 (2017).
Zilberberg et al., "*Clostridium difficile* Infections among Hospitalized Children, United States, 1997-2006," Emerg. Infect. Dis, 16(4):604-609 (2010).
Zilberberg et al., "Clostridium difficile-related Hospitalizations among US Adults, 2006," *Emerg. Infect. Dis*, 15(1):122-124 (2009).
Zilberberg et al., "Increase in Adult Clostridium difficile-related Hospitalizations and Case-Fatality Rate, United States, 2000-2005," *Emerg. Infect. Dis*, 14(6):929-931 (2008).
Zilberberg et al., "Increase in Clostridium difficile-related Hospitalizations Among Infants in the United States, 2000-2005," *Pediatr Infect Dis J.*, 27(12):1111-1113 (2008).
Zoppi et al., "Oral Bacteriotherapy in Clinical Practice," Eur J. Pediatr, 139(1):18-21 (1982).

(56) References Cited

OTHER PUBLICATIONS

Zoppi et al., "Oral Bacteriotherapy in Clinical Practice," Eur J. Pediatr, 139(1):22-24 (1982).

Zoppi et al., "The Intestinal Ecosystem in Chronic Functional Constipation," ACTA Paediatr, Scandinavian University Press, p. 836-841 (1998).

Khan et al ., "Antioxidants Keep the Potentially Probiotic but Highly oxygen-sensitive Human Gut Bacterium *Faecalibacterium prausnitzii* Alive at Ambient Air," 9(5)(e96097).

Marteau, P, et al., "Comparative study of bacterial groups within the human cecal and fecal microbiota", *Applied and Environmental Microbiology*, 67(10):4939-4942 (2001).

Unknown: "Anaerocult® P", Merck, Oct. 17, 2008 (Oct. 17, 2008), Retrieved from the Internet: URL:http://www.merckmillipore.com/NL/en/producVAnaerocult-P,MDA_CHEM-113807?ReferrerURL=https%3A%2F%2Fwww.google.com%2F [retrieved on May 3, 2019].

Unknown: : "GasPak System," (Sep. 28, 2009), Retrieved from the Internet: URL: https://web.archive.org/web/20090928043031/http://ftp.ccccd.edu/dcain/CCCCD%20Micro/gaspakjar.htm.

COMPOSITIONS FOR FECAL FLORAL TRANSPLANTATION AND METHODS FOR MAKING AND USING THEM AND DEVICES FOR DELIVERING THEM

CROSS-REFERENCE TO RELATED APPLICATIONS

This application is a continuation of U.S. patent application Ser. No. 16/523,726, filed on Jul. 26, 2019, which is a continuation of U.S. patent application Ser. No. 16/433,437, filed Jun. 6, 2019, which is a continuation of U.S. patent application Ser. No. 16/364,144, filed Mar. 25, 2019, which is a continuation of U.S. patent application Ser. No. 16/118,400, filed Aug. 30, 2018, (now U.S. Pat. No. 10,278,997, issued May 7, 2019), which is a continuation of U.S. patent application Ser. No. 15/975,456, filed May 9, 2018, which is a continuation of U.S. patent application Ser. No. 15/950,939, filed Apr. 11, 2018, (now U.S. Pat. No. 10,064,899, issued Sep. 4, 2018), which is a continuation of U.S. patent application Ser. No. 15/782,519, filed Oct. 12, 2017 (now U.S. Pat. No. 9,962,413, issued May 8, 2018), which is a continuation of U.S. patent application Ser. No. 15/093,679, filed Apr. 7, 2016 (now U.S. Pat. No. 10,022,406, issued Jul. 17, 2018), which is a continuation of U.S. patent application Ser. No. 13/813,915, filed Apr. 8, 2013 (now U.S. Pat. No. 9,308,226, issued Apr. 12, 2016), which is a U.S. National Stage of International Application No. PCT/AU2011/000987, filed Aug. 4, 2011, which claims priority to U.S. Provisional Application No. 61/494,363, filed Jun. 7, 2011, U.S. Provisional Application No. 61/483,487, filed May 6, 2011, U.S. Provisional Application No. 61/451,087, filed Mar. 9, 2011, U.S. Provisional Application No. 61/450,099, filed Mar. 7, 2011, and Australian Patent Application No. 2010903474, filed Aug. 4, 2010. All the foregoing mentioned applications are hereby incorporated by reference in their entirety.

TECHNICAL FIELD

This invention generally relates to medicine and gastroenterology, pharmacology and microbiology. In alternative embodiments, the invention provides compositions, e.g., formulations or preparations, and devices, used for the transplantation of a treated or isolated fecal flora, and methods for making and using them. In alternative embodiments, compositions, devices and methods of the invention can be used for any gastric, gastrointestinal and or colonic treatment or lavage. In alternative embodiments, compositions, devices and methods of the invention are used for the amelioration, stabilization, treatment and/or prevention of a disease or a condition such as constipation, Crohn's Disease, exposure to a poison or a toxin or for an infection, e.g., a toxin-mediated traveller's diarrhea; or any bowel disease or condition having a bowel dysfunction component, for example, an inflammatory bowel disease (IBD), Crohn's disease, hepatic encephalopathy, enteritis, colitis, irritable bowel syndrome (IBS), fibromyalgia (FM), chronic fatigue syndrome (CFS), depression, attention deficit/hyperaclivity disorder (ADHD), multiple sclerosis (MS), systemic lupus erythematosus (SLE), travellers' diarrhea, small intestinal bacterial overgrowth, chronic pancreatitis, or a pancreatic insufficiency, in alternative embodiments, the invention provides pharmaceuticals and products (articles) of manufacture for delivering these compositions and formulations to an individual, e.g., a human or an animal. The invention also provides devices for delivering a fecal material to an individual, e.g., a patient.

BACKGROUND

Bacterial flora of the bowel has recently gained importance from a therapeutic point of view. It is now realized that the human flora, rather than just being waste material resulting from digestion of food, is an important virtual organ containing large numbers of living microorganisms. There are in excess of one hundred thousand different subspecies—or more—arranged in families and subgroups of genetically different but often linearly related organisms. The waste "material" makes up a proportion of the flora. The bacterial content of the flora is actively breaking down or metabolizing the non-absorbed matter, largely fiber, on which the bacterial cells grow. Because the bacterial flora is contained within the human body and is made up of living components it constitutes in fact as a living organ or a virtual organ.

This virtual organ can be healthy in that it doesn't contain any pathogenic organisms, or it can become infected or infested with parasite, bacteria or viruses. When infected with some pathogenic species, such infecting species can manufacture molecules that affect secretion, which can cause pain, or can paralyze the bowel causing constipation. Infection of the bowel flora or bowel flora organ can impact the health of the individual.

Many of these infections can be acute, such as cholera, but some can be chronic and can really impact on the life of the individual carrying the infected flora. For example, after antibiotic therapy some of the families of the bacteria can be suppressed or eradicated and infectious agents such as *Clostridium difficile* and other pathogens can lodge and become passengers within the human flora. These 'passengers' are also pathogenic because they can produce toxins e.g. toxins A and B for *C. difficile*.

Definitions

The following are some definitions that may be helpful in understanding the description of the present invention. These are intended as general definitions and should in no way limit the scope of the present invention to those terms alone, but are put forth for a better understanding of the following description.

Unless the context requires otherwise or specifically stated to the contrary, integers, steps or elements of the invention recited herein as singular integers, steps or elements clearly encompass both singular and plural forms of the recited integers, steps or elements.

Throughout this specification, unless the context requires otherwise, the word "comprise", or variations such as comprises or "comprising", will be understood to imply the inclusion of a stated step or element or integer or group of steps or elements or integers, but not the exclusion of any other step or element or integer or group of elements or integers. Thus, in the context of this specification, the term "comprising" means "including principally, but not necessarily solely".

SUMMARY

According to a first aspect of the present invention, there is provided a delivery vehicle, formulation, composition, pharmaceutical preparation, product of manufacture, container or device, comprising: an entire (or substantially entire) microbiota; a treated or untreated fecal flora; a complete or partial fecal flora, a fecal flora substantially or completely purified of non-fecal floral fecal material, or a partially, substantially or completely isolated or purified fecal flora, made by a process comprising:

(i) providing an entire (or substantially entire) microbiota, a treated or untreated fecal flora sample, a complete or partial fecal flora sample, a fecal flora substantially or completely purified of non-fecal floral fecal material or a partially, substantially or completely isolated or purified fecal flora; and, a delivery vehicle, formulation, pharmaceutical preparation, composition, product of manufacture, container or device, and (ii) placing the entire (or substantially entire) microbiota, the treated or untreated fecal flora sample, the complete or partial fecal flora sample, the fecal flora substantially or completely purified of non-fecal floral fecal material, or the partially, substantially or completely isolated or purified focal flora in the delivery vehicle, formulation, composition, pharmaceutical preparation, product of manufacture, container or device.

According to a second aspect of the present invention, there is provided a product (article) of manufacture comprising a delivery vehicle, formulation, composition pharmaceutical preparation, container or device of the first aspect.

According to a third aspect of the present invention, there is provided a method for making a delivery vehicle, formulation, composition pharmaceutical preparation, product of manufacture, container or device according to the first or second aspect comprising (i) providing: an entire (or substantially entire) microbiota; a treated or untreated fecal sample; a complete or partial fecal flora sample, a fecal flora substantially or completely purified of non-fecal floral fecal material or a partially, substantially or completely isolated or purified fecal flora; and, a delivery vehicle, formulation, pharmaceutical preparation, composition product of manufacture, container or device, and (ii) placing the entire (or substantially entire) microbiota, treated or untreated fecal per sample, the complete or partial fecal flora, the fecal flora substantially or completely purified of nor-focal floral fecal material or the partially, substantially or completely isolated or purified fecal flora in the delivery vehicle, formulation, pharmaceutical preparation, composition, product of manufacture, container or device, and creating a substantially or completely oxygen-free environment in the container or device.

Aerating to a fourth aspect of the present invention there is provided a method for the amelioration, stabilization, treatment and/or prevention of an infection, disease, treatment, poisoning or a condition having a bowel dysfunction component or side-effect, or for the amelioration, treatment and/or prevention of a constipation, for the treatment of an abdominal pain, a non-specific abdominal pain or a diarrhea, a diarrhea caused by: a drug side effect of a psychological condition or Crohn's Disease, a poison, a toxin or an infection, a toxin-mediated travelers diarrhea, or a *Clostridium* or a *C. pertringens welchii* or a *C. difficile* infection or a pseudo-membranous colitis associated with a *Clostridium* infection, comprising:

administering to an individual in need thereof via a delivery vehicle, formulation, composition, pharmaceutical preparation, product of manufacture, container or device of the first aspect, or a product (article) of manufacture of the second aspect the entire (or substantially entire) microbiota, the treated or untreated fecal flora sample, the complete or partial fecal flora sample, the fecal flora substantially or completely purified of non-fecal floral fecal material, or the partially, substantially or completely isolated or purified fecal flora.

According to a fifth aspect of the present invention, there is provided a delivery vehicle, formulation, composition, pharmaceutical preparation, product of manufacture, container or device comprising:

an entire (or substantially entire) microbiota; a partially, substantially or completely isolated or purified fecal flora; or, a composition comprising a fecal flora substantially or a completely purified non-fecal floral fecal material.

According to a sixth aspect of the present invention, there is provided a method for the amelioration, stabilization, treatment and/or prevention of an infection, disease, treatment, poisoning or a condition having a bowel dysfunction component or side-effect comprising administering to an individual in need thereof via a delivery vehicle, formulation, composition, pharmaceutical preparation, product of manufacture, container or device according to the fifth aspect the entire (or substantially entire) microbiota, the partially, substantially or completely isolated or purified fecal flora, or the composition comprising a fecal flora substantially or a completely purified of non-fecal floral fecal material.

According to a seventh aspect of the present invention, there is provided a device for delivering a fecal material or a composition of the first aspect, comprising:

(a) a device as illustrated in FIG. 1B or FIG. 2; or (b) a device comprising (i) a bag or container comprising an exit aperture operably connected to the proximal end of a flexible tube or equivalent, (ii) an open or close valve or equivalent or an obturator screwtop at the distal end of the flexible tube or equivalent, and (iii) a pump, or a hand pump, for moving material in the bag or container through the flexible tube or equivalent and out the distal end or out the open or close valve of equivalent; or (c) the device of (a) or (b), further comprising a fecal material or a composition of the first aspect.

According to an eighth aspect of the present invention, there is provided a bag or container comprising: an entire (or substantially entire) microbiota; a treated or untreated fecal flora; a complete or partial fecal flora, a fecal flora substantially or completely purified of non-feral floral material or, a partially, substantially or completely isolated or purified fecal flora, or a composition thereof wherein the bag or container is structurally the same as or similar to a bag or container of a device of the seventh aspect.

According to a ninth aspect of the present invention, there is provided a method for the amelioration, stabilization, treatment and/or prevention of, or decreasing or delaying the symptoms of, an infection, disease, treatment, poisoning or a condition having a bowel dysfunction component or side-effect, or for the amelioration, treatment and/or prevention of a constipation, for the treatment of an abdominal pain, a non-specific abdominal pain or a diarrhea, a diarrhea caused by: a drug side effect or a psychological condition or Crohn's Disease, a poison, a toxin or an infection, a toxin-mediated traveller's diarrhea, or a *Clostridium* or a *C. perfringens welchii* or a *C. difficile* infection or a pseudo-membranous colitis associated with a *Clostridium* infection, or for preventing, or decreasing or delaying the symptoms of, or ameliorating or treating individuals with spondyloarthropathy, spondylarthritis or sacrolileitis (an inflammation of one or both sacroiliac joints); a nephritis syndrome; an inflammatory or an autoimmune condition having a gut or an intestinal component; lupus; irritable bowel syndrome on or spastic colon); or a colitis; Ulcerative Colitis or Crohn's Colitis; constipation; autism; a degenerative neurological diseases; amyotrophic lateral sclerosis (ALS), Multiple Sclerosis (MS) or Parkinson's Disease (PD); a Myoclonus Dystonia; Steinert's disease; proximal myotonic myopathy; an autoimmune disease; Rheumatoid Arthritis (RA) or juvenile idiopathic arthritis (JIA); Chronic Fatigue Syndrome; benign myalgic encephalomyelitis; chronic fatigue immune dysfunction syndrome; chronic infectious mononucleosis; epidemic myalgic encephalomyelitis; obesity; hypoglycemia, pre-diabetic syndrome, type I diabetes or type II diabetes; Idiopathic thrombocytopenic purpura (ITP); an acute or chronic allergic reaction; hives, a rash, a urticaria or a chronic urticaria; and/or insomnia or chronic insomnia, Grand mal seizures or petit mal seizures, comprising:

administering to an individual in need thereof via a delivery vehicle, formulation, pharmaceutical preparation, product of manufacture, container or device of the first aspect or a product (article) of manufacture of the second aspect of the entire (or substantially entire) microbiota, the treated or untreated fecal flora sample, the complete or partial fecal flora sample, the fecal flora substantially or completely purified of non-fecal floral fecal material, or the partially, substantially or completely isolated or purified fecal flora, in single, repeat or multiple administrations, deliveries or infusions.

According to a tenth aspect of the present invention, there is provided an entire (or substantially entire) microbiota, a treated or untreated fecal flora sample, a complete or partial fecal flora sample, a fecal flora substantially or completely purified of non-fecal floral fecal material, or a partially, substantially or completely isolated or purified fecal flora for use in the amelioration, stabilization, treatment and/or prevention of an infection, disease, treatment, poisoning or a condition having a bowel dysfunction component or side-effect, or for the amelioration, treatment and/or prevention of a constipation, for the treatment of an abdominal pain, a non-specific abdominal pain or a diarrhea, a diarrhea caused by: a drug side effect or a psychological condition or Crohn's Disease, a poison, a toxin or an infection, a toxin-mediated traveler's diarrhea, or a *Clostridium* or a *C. perfringens welchii* or a *C. difficile* infection or a pseudo-membranous colitis associated with a *Clostridium* infection.

According to an eleventh aspect of the present invention, there is provided use of an entire (or substantially entire) microbiota, a treated or untreated fecal flora sample, a complete or partial fecal flora sample, a fecal flora substantially or completely purified of non-fecal floral fecal material, or a partially, substantially or completely isolated or purified fecal flora in the preparation of a medicament for the amelioration, stabilization, treatment and/or prevention of an infection, disease, treatment, poisoning or a condition having a bowel dysfunction component or side-effect or for the amelioration, treatment and/or prevention of a constipation, for the treatment of an abdominal pain, a non-specific abdominal pain or a diarrhea, a diarrhea caused by: a drug side effect or a psychological condition or Crohn's Disease, a poison, a toxin or an infection, a toxin-mediated travelers diarrhea, or a *Clostridium* or a *C. perfringens welchii* or a *C. difficile* infection or a pseudo-membranous colitis associated with a *Clostridium* infection.

According to a twelfth aspect of the present invention, there is provided use of a device of the seventh aspect for delivering a fecal material or an entire (or substantially entire) microbiota, a treated or untreated fecal flora sample, a complete or partial fecal flora sample, a fetal flora substantially or completely purified of non-fecal floral fecal material, or a partially, substantially or completely isolated or purified fecal flora in the amelioration, stabilization, treatment and/or prevention of an infection, disease, treatment, poisoning or a condition having a bowel dysfunction component or side-effect, or for the amelioration, treatment and/or prevention of a constipation, for the treatment of an abdominal pain, a non-specific abdominal pain or a diarrhea, a diarrhea caused by: a drug side effect or a psychological condition or Crohn's Disease, a poison, a toxin or an infection, a toxin-mediated traveler's diarrhea, or a *Clostridium* or a *C. perfringens welchii* or a *C. difficile* infection or a pseudo-membranous colitis associated with a *Clostridium* infection.

In alternative embodiments, the invention provides compositions (including formulations, pharmaceutical compositions, foods, feeds, supplements, products of manufacture, and the like) comprising: delivery vehicle, formulation, container or device, comprising a treated or untreated fecal flora, or a partial, substantially or completely isolated fecal flora; and methods of making and using them.

In alternative embodiments, the invention provides delivery vehicles, formulations, pharmaceutical preparations, products of manufacture, containers or devices, comprising: a treated or untreated fecal flora, an entire (or substantially entire) microbiota, and/or a partially, substantially or completely isolated fecal flora, made by a process comprising:

(a) (i) providing a treated or untreated fecal sample, or a sample comprising an entire (or substantially entire) microbiota, or a composition comprising a complete or partial fecal flora, or a partially, substantial)/or completely isolated or purified fecal flora; and, a delivery vehicle, formulation, pharmaceutical preparation, product of manufacture, container or device, and (ii) placing the treated or untreated fecal sample, the partially, substantially or completely isolated or purified fecal flora, the entire (or substantially entire) microbiota, or a composition comprising a complete or partial fecal flora or partially, substantially or completely isolated or purified fecal flora, in the delivery vehicle, formulation, pharmaceutical preparation, product of manufacture, container or device, and optionally mating a substantially or completely oxygen-free environment in the delivery vehicle, formulation, pharmaceutical preparation, product of manufacture, container or device, and optionally the delivery vehicle, formulation, pharmaceutical preparation, product of manufacture, container or device is sterile or bacteria-free before the placing of the treated or untreated fecal sample, or the partially, substantially or completely isolated or purified fecal flora;

(b) the delivery vehicle, formulation, pharmaceutical preparation, product of manufacture, container or device of (a), wherein the delivery vehicle, formulation, pharmaceutical preparation, product of manufacture, container or device is made substantially or completely oxygen free (e.g., at least about 90%, 91%, 92%, 93%, 94%, 95%, 96%, 97%, 98%, 99%, 99.5%, 99.6%, 99.7%, 99.8% or 99.9% oxygen free) by: incorporating into the delivery vehicle, formulation, pharmaceutical preparation, product of manufacture, container or device a built in or clipped-on oxygen-scavenging mechanism; and/or, the delivery vehicle, formulation, pharmaceutical preparation, product of manufacture, container or device comprises or is coated with an oxygen scavenging material; and/or completely or substantially replacing the air in the delivery vehicle, formulation, pharmaceutical preparation, product of manufacture, container or device with nitrogen and/or other inert non-reactive gas or gases;

(c) the delivery vehicle, formulation, pharmaceutical preparation, product of manufacture, container or device of (a) or (b), wherein the delivery vehicle, formulation, pharmaceutical preparation, product of manufacture, container or device simulates (creates) partially, substantially or completely an anaerobic environment;

(d) the delivery vehicle, formulation, pharmaceutical preparation, product of manufacture, container or device of any, of (a) to (c), wherein the delivery vehicle, formulation, pharmaceutical preparation, product of manufacture, container or devise is manufactured, labelled or formulated for human or animal use;

(e) the delivery vehicle, formulation, pharmaceutical preparation, product of manufacture, container or device of (d), wherein the animal use is for a veterinary use;

(f) the delivery vehicle, formulation, pharmaceutical preparation, product of manufacture, container or device of any of (a) to (e), wherein a stabilizing agent or a glycerol is added to, or mixed into, the treated or untreated fecal sample, entire (or substantially entire) microbiota, or partially, substantially or completely isolated fecal flora, before storage or freezing, spray-drying, freeze-drying or lyophilizing;

(g) the delivery vehicle, formulation, pharmaceutical preparation, product of manufacture, container or device of any of (a) to (f), wherein the delivery vehicle, formulation, pharmaceutical preparation, product of manufacture, container or device is initially manufactured or formulated as a liquid, a suspension, a gel, a geltab, a semisolid, a tablet, a sachet, a lozenge or a capsule, or as an enteral formulation, or re-formulated for final delivery as a liquid, a suspension, a gel, a geltab, a semisolid, a tablet, a sachet, a lozenge or a capsule, or as an enteral formulation;

(h) the delivery vehicle, formulation, pharmaceutical preparation, product of manufacture, container or device of any of (a) to (g), wherein the fecal sample is treated such that the fecal flora is separated from rough particulate matter in the fecal sample by: homogenizing, centrifuging and/or filtering a rough particulate matter or a non-floral matter of the fecal material, or by plasmapheresis, centrifugation, celltrifuge, column chromatography (e.g., affinity chromatography), immunoprecipitation (e.g., antibodies fixed to a solid surface, such as beads or a plate);

(i) the delivery vehicle, formulation, pharmaceutical preparation, product of manufacture, container or device of any of (a) to (h), wherein the treated or untreated fecal flora, entire (or substantially entire) microbiota, or partially, substantially or completely isolated or purified fecal flora, is lyophilized, freeze-dried or frozen, or processed into a powder;

(j) the delivery vehicle, formulation, pharmaceutical preparation, product of manufacture, container or device of any of (a) to (i), wherein the fecal flora (including e.g., the entire (or substantially entire) microbiota) is initially derived from an individual screened or tested for a disease or infection, and/or the fecal flora is initially derived from an individual screened to have a normal, healthy or wild type population of fecal flora;

(k) the delivery vehicle, formulation, pharmaceutical preparation, product of manufacture, container or device of any of (a) to (j), wherein a substantially isolated or a purified fecal flora or entire (or substantially entire) microbiota is (comprises) an isolate of fecal flora that is at least about 90%, 91%, 92%, 93%, 94%, 95%, 96%, 97%, 98%, 99%, 99.5%, 99.6%, 99.7%, 99.8% or 99.9% isolated or pure, or having no more than about 0.1%, 0.2%, 0.3%, 0.4%, 0.5%, 0.8%, 0.7%, 0.8%, 0.9% or 1.0% or more non-fecal floral material; or (l) the delivery vehicle, formulation, pharmaceutical preparation, product of manufacture, container or device of any of (a) to (j), wherein the amount of the treated or untreated fecal sample, entire (or substantially entire) microbiota, or the partially, substantially or completely isolated or purified fecal flora is formulated for or calibrated for repeat or multiple delivery or infusions, wherein optionally the repeated or multiple administration, delivery, infusion or implantation protocol comprises infusions done daily for the first about 10 days, second daily for about 10 days, third daily then fourth daily possibly weekly and then optionally maintain second or more weekly infusions until the histology reverses towards normality.

In alternative embodiments, the delivery vehicle, formulation, pharmaceutical preparation, product of manufacture, container or device of the invention further comprises:

a saline, a media, a defoaming agent, a surfactant agent, a lubricant, an add neutralizer, a marker, a cell marker, a drug, an antibiotic, a contrast agent, a dispersal agent, a buffer or a buffering agent, a sweetening agent, a debittering agent, a flavouring agent, a pH stabilizer, an acidifying agent, a preservative, a desweetening agent and/or colouring agent;

at least one vitamin, mineral and/or dietary supplement, wherein optionally the vitamin comprises a thiamine, riboflavin, nicotinic acid, pantothenic add, pyridoxine, biotin, folic acid, vitamin $B_{12}$, lipoic acid, ascorbic acid, vitamin A, vitamin D, vitamin E, vitamin K, a choline, a carnitine, and/or an alpha, beta and/or gamma carotene; or a prebiotic nutrient, wherein optionally the prebiotic comprises any ingredient that stimulates the stability, growth and/or activity of the fecal flora or fecal bacteria, or optionally comprises polyols, fructooligosaccharides (FOSs), oligofructoses, insulins, galactooligosaccharides (GOSs), xylooligosaccharides (XOSs), polydextroses, monosaccharides, tagatose, and/or mannooligosaccharides.

In alternative embodiments, the invention provides products (articles) of manufacture comprising a delivery vehicle, formulation, pharmaceutical preparation, container or device of the invention.

In alternative embodiments, the invention provides methods for making a delivery vehicle, formulation, pharmaceutical preparation, product of manufacture, container or device, comprising a treated or untreated fecal flora, entire (or substantially entire) microbiota, or a partially, substantially or completely isolated or purified fecal flora, comprising:

(a) (i) providing a treated or untreated fecal sample, or a composition comprising a complete or partial fecal flora, an entire (or substantially entire) microbiota, or a partially, substantially or completely isolated or purified fecal flora; and, a delivery vehicle, formulation, pharmaceutical preparation, product of manufacture, container or device, and (ii) placing the treated or untreated fecal sample, the partially, substantially or completely isolated or purified fecal flora, the entire (or substantially entire) microbiota, or a composition comprising a complete or partial fecal flora or partially, substantially or completely isolated or purified fecal flora, in the delivery vehicle, formulation, pharmaceutical preparation, product of manufacture, container or device, and creating a substantially or completely oxygen-free environment in the container or device;

(b) the method of (a), wherein the delivery vehicle, formulation, pharmaceutical preparation, product of manufacture, container or device is made substantially or completely oxygen free by: incorporating into the delivery vehicle, formulation, container or device a built in or clipped-on oxygen-scavenging mechanism; and/or, the delivery vehicle, formulation, pharmaceutical preparation, product of manufacture, container or device comprises or is coated with an oxygen scavenging material; and/or completely or substantially replacing the air in the delivery vehicle, formulation, pharmaceutical preparation, product of manufacture, container or device with nitrogen and/or other inert non-reactive gas or gases;

(c) the method of (a) or (b), wherein the delivery vehicle, formulation, pharmaceutical preparation, product of manufacture, container or device simulates (creates) partially, substantially or completely an anaerobic environment;

(d) the method of any of (a) to (c), wherein the delivery vehicle, formulation, pharmaceutical preparation, product of manufacture, container or device is manufactured, labelled or formulated for human or animal use;

(e) the method of (d), wherein the animal use is for a veterinary use;

(f) the method of any of (a) to (e), wherein a prebiotic, a stabilizing agent or a glycerol is added to, or mixed into, the treated or untreated fecal sample, or partially, substantially or completely isolated or purified fecal flora, before storage or freeze-drying, spray-drying, freezing or lyophilizing;

(g) the method of any of (a) to (f), wherein the delivery vehicle, formulation, pharmaceutical preparation, product of manufacture, container or device is initially manufactured or formulated as a liquid, a suspension, a gel, a geltab, a semisolid, a tablet, a sachet, a lozenge or a capsule, or as an enteral formulation, or re-formulated for final delivery as a liquid, a suspension, a gel, a geltab, a semisolid, a tablet, a sachet, a lozenge or a capsule, or as an enteral formulation;

(h) the method of any of (a) to (g), wherein the fecal sample is treated such that the fecal flora is separated from rough particulate matter in the fetal sample by: homogenizing, centrifuging and/or filtering a rough particulate matter or a roll-floral matter of the fecal material, or by plasmapheresis, centrifugation, centrifuge, column chromatography (e.g., affinity chromatography), immunoprecipitation (e.g., antibodies fixed to a solid surface, such as beads or a plate);

(i) the method of any of (a) to (h), wherein the treated or untreated fecal flora, or partially, substantially or completely isolated or purified fecal flora, is lyophilized, freeze-dried or frozen, or processed into a powder;

(j) the method of any of (a) to (i), wherein the fecal flora is initially derived from an w individual screened or tested for a disease or infection, and/or the fecal flora is initially derived from an individual screened to have a normal, healthy or wild type population of fecal flora; or (k) the method of any of (a) to (j), further comprising adding to the treated or untreated fecal flora, or adding to a liquid or solution used to isolate or purify, store, freeze, freeze-dry, sprain dry, lyophilize, transport, reconstitute and/or deliver a treated or untreated fecal flora (optionally an entire (or substantially entire) microbiota, a partially, substantially or completely isolated or purified fecal flora, or a composition comprising a fecal flora substantially or completely purified of non-fecal floral fecal material of the invention):

a saline, a media, a defoaming at a surfactant agent, a lubricant, an acid neutralizer, a marker, a cell marker, a drug, an antibiotic, a contrast agent, a dispersal agent, a buffer or a buffering agent, a sweetening agent, a debittering agent, a flavouring agent, a pH stabilizer, an acidifying agent, a preservative, a desweetening agent and/or colouring agent, and/or at least one vitamin, mineral and/or dietary supplement, wherein optionally the vitamin comprises a thiamine, riboflavin, nicotinic acid, pantothenic acid, pyridoxine, biotin, folic add, vitamin $B_{12}$, lipoic acid, ascorbic acid, vitamin A, vitamin D, vitamin E, vitamin K, a choline, a carnitine, and/or an alpha, beta end/or gamma carotene, and/or a prebiotic nutrient, wherein optionally the prebiotic comprises any ingredient that stimulates the stability, growth and/or activity of the fecal flora or fecal bacteria, or optionally comprises polyols, fructooligosaccharides (FOSs), oligofructoses, insulins, galactooligosaccharides (GOSs), xylooligosaccharides (XOSs), polydextroses, monosaccharides, tagatose, and/or mannooligosaccharides;

(l) the method of any of (a) to (k), wherein an entire (or substantially entire) microbiota, a substantially isolated or a purified fecal flora is (comprises) an isolate of fecal flora that is at least about 90%, 91%, 92%, 93%, 94%, 95%, 98%, 97%, 98%, 99%, 99.5%, 99.6%, 99.7%, 993% or 99.9% isolated or pure, or having no more than about 0.1%, 0.2%, 0.3%, 0.4%, 0.5%, 0.6%, 0.7%, 0.8%, 0.9% or 1.0% or more non-fecal floral material; or (m) the method of any of (a) to (l), wherein the amount of the entire (or substantially entire) microbiota, the treated or untreated fecal sample, or the partially, substantially or completely isolated or purified fecal flora is formulated for or calibrated for repeat or multiple delivery or infusions, wherein optionally the repeated or multiple administration, delivery, infusion or implantation protocol comprises infusions done daily for the first about 10 days, second daily for about 10 days, third daily then fourth daily possibly weekly and then optionally maintain second or more weekly infusions until the histology reverses towards normality.

In alternative embodiments, the invention provides methods for the amelioration, stabilization, treatment and/or prevention of an infection, disease, treatment, poisoning or a condition having a bowel dysfunction component or side-effect, or for the amelioration, stabilization, treatment and/or prevention of a constipation, for the treatment of an abdominal pain, a non-specific abdominal pain or a diarrhea, a diarrhea caused by: a drug side effect or a psychological condition or Crohn's Disease, a poison, a toxin or an infection, a toxin-mediated traveller's diarrhea, or a *Clostridium* or a *C. difficile* or a pseudo-membranous colitis associated with a *Clostridium* infection, comprising administering to an individual in need thereof a delivery vehicle, formulation, pharmaceutical preparation, product of manufacture, container or device of the invention, or a product (article) of manufacture of the invention.

In alternative embodiments, the invention provides methods for the amelioration, stabilization, treatment and/or prevention of an infection, disease, treatment, poisoning or a condition having a bowel dysfunction component or side-effect comprising administering to an individual in need thereof a delivery vehicle, formulation, pharmaceutical preparation, product of manufacture, container or device of the invention, or a product (article) of manufacture of the invention, or their contents (e.g., the bacterial flora contained therein).

In alternative embodiments, the amount of the treated or untreated fecal sample, or the partially, substantially or completely isolated or purified fecal flora is formulated for or calibrated for repeat or multiple delivery or infusions; or the partially, substantially or completely isolated or purified fecal flora is delivered in repeated or multiple infusions, wherein optionally the repeated or multiple administration, delivery, infusion or implantation protocol comprises infusions done daily for the first about 10 days, second daily for about 10 days, third daily then fourth daily possibly weekly and then optionally maintain second or more weekly infusions until the histology reverses towards normality.

In alternative embodiments, of the methods the infection, disease, treatment, poisoning or condition having a bowel dysfunction component or side-effect comprises an inflammatory bowel disease (IBD), Crohn's disease, hepatic encephalopathy, enteritis, colitis, irritable Bowel Syndrome (IBS), fibromyalgia (FM), chronic fatigue syndrome (CFS), depression, attention deficit/hyperactivity disorder (ADHD), multiple sclerosis (MS), systemic lupus erythematosus (SLE), travellers' diarrhea, small intestinal bacterial overgrowth, chronic pancreatitis, a pancreatic insufficiency, exposure to a poison or a toxin or for an infection, a toxin-mediated traveller's diarrhea, a poisoning, a pseudomembranous colitis, a *Clostridium* infection, a *C. perfringens welchii* or a *Clostridium difficile* infection, a neurological condition, Parkinson's disease, myoclonus dystonia, autism, amyotrophic lateral sclerosis, multiple sclerosis, Grand mal seizures or petit mal seizures. In alternative embodiments, the amount of the treated or untreated fecal sample, or the partially, substantially or completely isolated or purified fecal flora, is formulated for or calibrated for repeat of multiple delivery or infusions; or the treated or untreated fecal sample or the partially, substantially or completely isolated or purified fecal flora is delivered in repeated or multiple infusions, wherein optionally the repeated or multiple administration, delivery, infusion or implantation protocol comprises infusions done daily for the first about 10 days, second daily for about 10 days, third daily then fourth daily possibly weekly and then optionally maintain second or more weekly infusions until the histology reverses towards normality.

In alternative embodiments, the invention provides delivery vehicles, formulations, pharmaceutical preparations, products of manufacture, containers or devices comprising:

(a) an entire (or substantially entire) microbiota, a partially, substantially or completely isolated or purified fecal flora, or a composition comprising a fecal flora substantially or completely purified of non-fecal floral fecal material, and optionally further comprising an excipient, or a fluid, a saline, a buffer, a buffering agent or a media, or a fluid-glucose-cellobiose agar (RGCA) media;

(b) the composition, container or device, formulation, or product of manufacture of (a), wherein the entire (or substantially entire) microbiota or the fecal flora is isolated or purified from a human or an animal fecal material;

(c) the composition, container or device, formulation, or product of manufacture of (a) or (b), wherein the entire (or substantially entire) microbiota or the fecal flora is isolated or purified using a method or protocol comprising use of a centrifuge, a centrifuge, a column or an immuno-affinity column, or wherein the entire (or substantially entire) microbiota or the fecal flora is isolated or purified by a method comprising homogenizing, centrifuging and/or filtering a rough particulate matter or a non-floral matter of the focal material, or by plasmapheresis, centrifugation, centrifuge, column chromatography (e.g., affinity chromatography), immunoprecipitation (e.g., antibodies fixed to a solid surface, such as beads or a plate);

(d) the composition, container or device, formulation, or product of manufacture of any of (a) to (c), wherein the entire (or substantially entire) microbiota or the substantially or completely isolated or purified fecal flora, or the fecal flora substantially or completely purified of non-fecal floral fecal material, is in a substantially or completely oxygen-free environment in the composition, container or device, formulation, or product of manufacture;

(e) the delivery vehicle, formulation, container or device of (d), wherein the composition, container or device, formulation, or product of manufacture is made substantially or completely oxygen free by: incorporating into the delivery vehicle, formulation, container or device a built in or clipped-on oxygen-scavenging mechanism; and/or, the delivery vehicle, formulation, container or device comprises or is coated with an oxygen scavenging material; and/or completely or substantially replacing the air in the delivery vehicle, formulation, container or device with nitrogen and/or other inert non-reactive gas or gases;

(f) the composition, container or device, formulation, or product of manufacture of any of (a) to (c), wherein the entire (or substantially entire) microbiota, the substantially or completely isolated or purified fecal flora, or the fecal flora substantially or completely purified of non-fecal floral fecal material, is in a substantially or completely anaerobic environment;

(g) the composition, container or device, formulation, or product of manufacture of any of (a) to (f), wherein the delivery vehicle, formulation, container or vice is manufactured, labelled or formulated for human or animal use;

(h) the composition, container or device, formulation, or produce of manufacture of (g), wherein the animal use is for a veterinary use;

(i) the composition, container or device, formulation, or product of manufacture of any of (a) to (h), wherein a stabilizing agent or a glycerol is added to, or mixed into, the entire (or substantially entire) microbiota, or the partially, substantially or completely isolated or purified fecal flora, or the composition comprising a fecal flora substantially or completely purified of non-fecal floral fecal material, before storage or freezing, freeze-drying, spray-drying or lyophilizing;

(j) the composition, container or device, formulation, or product of manufacture of any of (a) to (f), wherein the composition, container or device, formulation, or product of manufacture is initially manufactured or formulated as a liquid, a suspension, a gel, a geltab, a semisolid, a tablet, a sachet, a lozenge or a capsule, or as an enteral formulation, or re-formulated for final delivery as a liquid, a suspension, a gel, a geltab, a semisolid, a tablet, a sachet, a lozenge or a capsule, or as an enteral formulation;

(k) the composition, container or device, formulation, or product of manufacture of any of (a) to (j) wherein the entire (or substantially entire) microbiota, or the partially, substantially or completely isolated or purified fecal flora, or The composition comprising a fecal flora substantially or completely purified of non-fecal floral fecal material, is lyophilized, freeze-dried, in powder form, or frozen;

(l) the composition, container or device, formulation, or product of manufacture of any of (a) to (k), wherein the entire (or substantially entire) microbiota or The fecal flora is initially derived from an individual screened or tested for a disease or infection, and/or the entire (or substantially entire) microbiota or the fecal flora is initially derived from an individual screened to have a normal, healthy or wild type population of fecal flora; or (m) the composition, container or device, formulation, or product of manufacture of any of (a) to (l), further comprising adding to the entire (or substantially entire) microbiota, the partially, substantially or completely isolated or purified fecal flora, or a composition comprising a fecal flora substantially or completely purified of non fecal floral fecal material, or adding to a liquid or solution used to isolate or purity, store, freeze, freeze-dry, spray-dry, lyophilize, transport, reconstitute and/or deliver a treated or untreated fecal flora:

a saline, a media, a defoaming agent, a surfactant agent, a lubricant, an acid neutralizer, a marker, a cell marker, a drug, an antibiotic, a contrast agent, a dispersal agent, a buffer or a buffering agent, a sweetening agent, a debittering agent, a flavouring agent, a pH stabilizer, an acidifying agent, a preservative, a desweetening agent and/or colouring agent, and/or at least one vitamin, mineral and/or dietary supplement, wherein optionally the vitamin comprises a thiamine, riboflavin, nicotinic acid, pantothenic acid, pyridoxine, biotin, folic acid, vitamin $B_{12}$, lipoic acid, ascorbic acid, vitamin A, vitamin D, vitamin E, vitamin K, a choline, a carnitine, and/or an alpha, beta and/or gamma carotene, and/or a prebiotic nutrient, wherein optionally the prebiotic comprises any ingredient that stimulates the stability, growth and/or activity of the entire (or substantially entire) microbiota or the fecal flora or fecal bacteria, or optionally comprises polyols, fructooligosaccharides (FOSs), oligofructoses, insulins, galactooligosaccharides (GOSs), xylooligosaccharides (XOSs), polydextroses, monosaccharides, tagatose, and/or mannooligosaccharides;

(n) the composition, container or device, formulation, or product of manufacture of any of (a) to (m), wherein a substantially mated or a purified fecal flora is (comprises) an isolate of the entire (or substantially entire) microbiota or fetal flora that is at least about 90%, 91%, 92%, 93%, 94%, 95%, 96%, 97%, 98%, 99%, 995%, 99.6%, 991%, 99.8% or 99.9% isolated or pure, or having no more than about 0.1%, 0.2%, 0.3%, 0.4%, 0.5%, 0.6%, 0.8%, 0.9% or 1.0% or more non-fecal floral material; or (m) the composition, container or device, formulation, or product of manufacture of any of (a) to (l), wherein the amount of the entire (or substantially entire) microbiota or the treated or untreated fecal sample, or the partially, substantially or completely isolated or purified fecal flora is formulated for or calibrated for repeat or multiple delivery or infusions, wherein optionally the repeated or multiple administration, delivery, infusion or implantation protocol comprises infusions done daily for the first about 10 days, second daily for about 10 days, third daily then fourth daily possibly weekly and then optionally maintain second or more weekly infusions until the histology reverses towards normality.

In alternative embodiments, the invention provides methods for the amelioration, stabilization, treatment and/or prevention of an infection, disease, treatment, poisoning or a condition having a bowel dysfunction component or side-effect comprising administering to an individual in need thereof a composition, container or device, formulation, or product of manufacture of the invention.

In alternative embodiments, of the methods the infection, disease, treatment, poisoning or condition having a bowel dysfunction component or side-effect comprises an inflammatory bowel disease (IED), Crohn's disease, hepatic encephalopathy, enteritis, colitis, irritable bowel syndrome (IES), fibromyalgia (FM), chronic fatigue syndrome (CFS), depression, attention deficit/hyperactivity disorder (ADHD), multiple sclerosis (MS), systemic lupus erythematosus (SLE), travellers' diarrhea, small intestinal bacterial overgrowth, chronic pancreatitis, a pancreatic insufficiency, exposure to a poison or a toxin or for an infection, a toxin-mediated traveller's diarrhea, a poisoning, a pseudomembranous colitis, a *Clostridium* infection, a *C. perfringens welchii* or a *Clostridium difficile* infection, a neurological condition, Parkinson's disease, myoclonus dystonia, autism, amyotrophic lateral sclerosis, multiple sclerosis, Grand mal seizures or petit mal seizures.

In alternative embodiments, the invention provides methods for the amelioration, stabilization, treatment and/or prevention of, or decreasing or delaying the symptoms of, an infection, disease, treatment, poisoning or a condition having a bowel dysfunction component or side-effect, or for the amelioration, treatment and/or prevention of a constipation, for the treatment of an abdominal pain, a non-specific abdominal pain or a diarrhea, a diarrhea caused by: a drug side effect or a psychological condition or Crohn's Disease, a poison, a toxin or an infection, a toxin-mediated traveller's diarrhea, or a *Clostridium* or a *C. perfringens welchii* or a *C. difficile* infection or a pseudo-membranous colitis associated with a *Clostridium* infection, or for preventing, decreasing or delaying the symptoms of, ameliorating stabilizing, or treating individuals (e.g., patients or animals) with spondyloarthropathy, spondylarthritis or sacrolileitis (an inflammation of one or both sacroiliac joints); a nephritis syndrome; an inflammatory or an autoimmune condition having a Gut or an intestinal component such as lupus, irritable bowel syndrome (IBS or spastic colon) or a colitis such as Ulcerative Colitis or Crohn's Colitis; constipation, autism; degenerative neurological diseases such as amyotrophic lateral sclerosis (ALS), Multiple Sclerosis (MS) or Parkinson's Disease (DR) a Myoclonus Dystonia (e.g., Steinert's disease or proximal myotonic myopathy); an autoimmune disease such as Rheumatoid Arthritis (RA) or juvenile idiopathic arthritis (JIA); Chronic Fatigue Syndrome (including benign myalgic encephalomyelitis, chronic fatigue immune dysfunction syndrome, chronic infectious mononucleosis, epidemic myalgic encephalomyelitis); obesity; hypoglycemia, prediabetic syndrome, type I diabetes or type II diabetes; Idiopathic thrombocytopenic purpura (ITP); an acute or chronic allergic reaction such as hives, a rash, a urticaria or a chronic urticaria; and/or insomnia or chronic insomnia, Grand mal seizures or petit mal seizures, comprising:

administering to an individual in need thereof a delivery vehicle, formulation, pharmaceutical preparation, product of manufacture, container or device of the invention, or a product (article) of manufacture of the invention, in single, repeat or multiple administrations, deliveries or infusions.

In alternative embodiments, the amount of the entire (or substantially entire) microbiota, the treated or untreated fecal sample, or the partially, substantially or completely isolated or purified fecal flora, is formulated for or calibrated for repeat or multiple delivery or infusions; or the entire (or substantially entire) microbiota, the treated or untreated fecal sample or the partially, substantially or completely isolated or purified fecal flora is delivered in repeated or multiple infusions, wherein optionally the repeated or multiple administration, delivery, infusion or implantation protocol comprises infusions done daily for the first about 10 days, second daily for about 10 days, third daily then fourth daily possibly weekly and then optionally maintain second or more weekly infusions until the histology reverses towards normality.

In alternative embodiments, the invention provides devices for delivering a (bacterial flora-comprising) composition of the invention, or an entire (or substantially entire) microbiota or a fecal material comprising:

(a) a device as illustrated in FIG. 1 or FIG. 2, or equivalent thereof; or (b) (1) a bag or container comprising an exit aperture operably connected to the proximal end of a flexible tube or equivalent, wherein the bag or container is optionally made of a material impervious to a gas or to oxygen, and optionally the bag or container is made of a flexible material, or a polyethylene terephthalate polyester film-comprising (or a MYLAR™-comprising) material, and optionally the bag or container is an (IV-like) intravenous-like bag, and optionally the bag or container has an attachment that will allow the bag to be hung on a stand, e.g., to be positioned/hung above an endoscope, and optionally the bag or container is operably connected via an open or Glow valve or equivalent to a negative pressure device that can remove all gas or air from the bag, and optionally the bag or container is operably connected via an open or close valve or equivalent to a fluid source or storage container for flushing out the bag through the exit aperture, end optionally the fluid source or storage container is under positive pressure, and optionally the flexible tube or equivalent comprises at least one clip or close valve or one way valve to prevent backwash of material from distal to proximal portions of the tube, or from the tube back to the bag or container;

(2) an open or close valve or equivalent or an obdurator screwtop at the distal end of the flexible tube or equivalent, and optionally a Luer lock tip for attachment to a colonoscope or an endoscopic Luer lock port or equivalent, wherein optionally the Luer lock tip is built into the valve, or is separate from the valve, and optionally an enema tube tip for attachment to an enema tube or device or equivalent, wherein optionally the enema tube tip is built into the valve, or is separate from the valve, and optionally further comprising a safety device or safety clip to close the distal aperture in case the valve or Luer lock tip, or enema tip, is lost (flies off) under pressure; and (3) a pump, or a hand pump, for moving material in the bag or container through the flexible tube or equivalent and out the distal end or out the open or close valve or equivalent; or (c) the device of (a) or (b), further comprising a fecal material or a composition of the invention.

In alternative embodiments, the invention provides bags or containers comprising an entire (or substantially entire) microbiota, or a treated or untreated fecal flora, or a partially, substantially or completely isolated fecal flora, or a composition of the invention (e.g., a formulation comprising an entire (or substantially entire) microbiota, a partially, substantially or completely isolated or purified fecal flora, or a composition comprising a fecal flora substantially or completely purified of non-fecal floral fecal material), and optionally further comprising an excipient, or a fluid, a saline, a buffer, a buffering agent or a media, or a fluid-glucose-cellobiose agar (RGCA) media, wherein the bag or container is structurally the same as or similar to a tag or container of a device of the invention (e.g., as illustrated in FIG. 1 or FIG. 2), wherein optionally the interior of the bag is substantially or completely an oxygen-free environment, or the interior of the bag is substantially or completely similar to an anaerobic environment.

In alternative embodiments, specific anti C. difficile oral antibodies (for example avian) can be added to a solution (e.g., a saline, media, buffer) used to isolate or purify, store, freeze, freeze-dry, spray-dry lyophilize, transport, reconstitute and/or deliver a composition (e.g., a partially, substantially or completely isolated or purified fecal flora, or a composition comprising a fecal flora substantially or completely purified of non-fecal floral fecal material) of the invention. The combination of the product with these specific anti C. difficile oral antibodies enhances the eradication mechanism of the product.

The details of one or more embodiments of the invention are set forth in the accompanying drawings and the description below. Other features, objects, and advantages of the invention will be apparent from the description and drawings, and fin the claims.

All publications, patents, patent applications cited herein are hereby expressly incorporated by reference for all purposes.

BRIEF DESCRIPTION OF THE DRAWINGS

The drawings set forth herein are illustrative of embodiments of the invention and are not meant to limit the scope of the invention as encompassed by the claims.

Figure 1A:
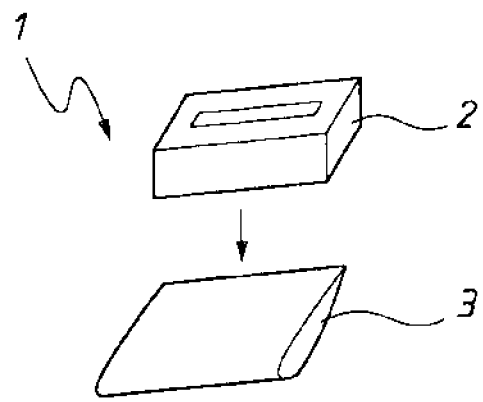
FIG. 1A illustrates an exemplary storage device of the invention; and, FIG. 1B illustrates an exemplar), delivery device of the invention, as described below.

Like reference symbols in the various drawings indicate like elements, Reference will now be made in detail to various exemplary embodiments of the invention, examples of which are illustrated in the accompanying drawings. The following detailed description is provided to give the reader a better understanding of certain details of aspects and embodiments of the inventions and should not be interpreted as a limitation on the scope of the invention.

DETAILED DESCRIPTION

In alternative embodiments, the invention provides compositions, e.g., formulations and pharmaceutical preparations, products of manufacture, and containers and delivery vehicles, and devices and delivery materials, comprising treated and/or isolated faecal (fecal) material for faecal floral transplantation. In one embodiment the treated and/or isolated fecal material of the invention comprising faecal floral (e.g., bacteria) is transplanted between different individuals, e.g., human to human or between animals. In one embodiment, the treated fecal material of the invention is transplanted back into the same individual from which it was collected, e.g., to repopulate a colon after drug treatment (e.g., antibiotic treatment or chemotherapy) or after an orthostatic lavage, e.g., for inducing the purgation (e.g., cleansing) of a gastrointestinal (GI) tract, including a colon.

The invention provides methods for the amelioration, stabilization, or treatment of a bowel disease or infection comprising use of a delivery vehicle, formulation, product of manufacture, or container or device of the invention; e.g., as a fecal bacteriotherapy, fecal transfusion, fecal transplant, or human probiotic infusion (HPI). In alternative embodiments, the invention provides methods for ameliorating, stabilizing, treating or preventing any infection, bowel disease or to condition having a bowel dysfunction component, for example, a poisoning, a pseudomembranous colitis, a *Clostridium difficile* infection, an inflammatory bowel disease (IBD), Crohn's disease, hepatic encephalopathy, enteritis, colitis, irritable bowel syndrome (IBS), fibromyalgia (FM), chronic fatigue syndrome (CFS), depression, attention deficit/hyperactivity disorder (ADHD), multiple sclerosis (MS), systemic lupus erythematosus (SLE), travellers' diarrhea, small intestinal bacterial overgrowth, chronic pancreatitis, or a pancreatic insufficiency.

For example, in one embodiment, as antibiotics do not eradicate *C. difficile* and its spore, a delivery vehicle, formulation, product of manufacture, or container or device of the invention comprising treated and/or isolated fecal flora can ameliorate, stabilize or eradicate *C. difficile* (or the pseudo-membranous colitis associated with this infection) when infused into a colon of the infected n or ill individual, e.g., a patient or animal. In alternative embodiments the fecal flora obtained from a donor (which in treated or isolated form is in alternative embodiments in a delivery vehicle, formulation, product of manufacture, or container or device of the invention) comprises a part of, substantially a of, or all of the infected or ill recipient's missing or inadequate (e.g., in numbers or function) fecal flora, e.g., bacteria. While the invention is not limited by any particular mechanism of action, in some embodiments it is the transfer of the equivalent of: a part of, substantially all of, or all of the fecal flora of the infected individual from the donor to the recipient (e.g., from human to human) that ameliorates or eradicates the infection or the pseudo-membranous colitis associated with this infection.

In alternative embodiments, the compositions, e.g., formulations and pharmaceutical preparations, and devices, delivery materials, delivery vehicles, products of manufacture, containers and devices of the invention allow the safe transplantation of fecal flora (e.g., human flora) components to individuals in need thereof, e.g., to infected, sick and dying patients, thus providing a consistently safe yet functioning flora for delivery to a recipient or patient.

In alternative embodiments, the invention provides a reliable method for producing standardized fresh fecal flora which can have a long shelf life. For example, in one embodiment, the delivery vehicle, formulation, pharmaceutical preparation, product of manufacture, container or device comprising the fecal flora comprises a substantially or completely oxygen-free environment. In another embodiment, nutrients such as prebiotic nutrients can be added (e.g., in dry or liquid forms) to a solution (e.g., a saline, media, buffer) used to isolate or purify, store, freeze, freeze-dry, spray-dry, lyophilize, transport, reconstitute and/or deliver a composition (e.g., a partially, substantially or completely isolated or purified fecal flora, or a composition comprising a fecal flora substantially or completely purified of non-fecal floral fecal material) of the invention. A prebiotic nutrient can be any ingredient that stimulates the stability, growth and/or activity of the fecal flora, e.g., bacteria; for example, in alternative embodiments, polyols, fructooligosaccharides (FOSs), oligofructoses, insulins, galactooligosaccharides (GOSs), xylooligosaccharides (XOSs), polydextroses, monosaccharides such as tagatose, and/or mannooligosaccharides are used as prebiotics to practice this invention. In one embodiment, the prebiotics are added to prevent "shock" to the fecal flora subsequent to their isolation or purification, freezing, freeze-drying, spray-drying, reconstitution in solution and the like.

In alternative embodiments, components of the compositions, e.g., delivery vehicles, formulations and pharmaceutical preparations, products of manufacture, or containers or devices, of the invention comprise an entire (or substantially entire) microbiota, or a *Bacteroides* and/or *Firmicutes* in large numbers (e.g., a larger proportion of *Bacteroides* and/or *Firmicutes* is present that is normally found in situ), e.g., to be able to ameliorate and/or eradicate a *C. difficile* infection and/or the pseudo-membranous colitis associated with this infection. In alternative embodiments, the compositions, e.g., delivery vehicles, formulations and pharmaceutical preparations, products of manufacture, or containers or devices, of the invention can be available (e.g., formulated and/or dosaged for) for recurrent use in individuals, e.g., in patients or animals, with the more difficult to treat conditions such as colitis (e.g., the pseudo-membranous colitis of a *C. difficile* infection) and constipation.

In alternative embodiments, components of the compositions e.g., delivery vehicles, formulations and pharmaceutical preparations, products of manufacture, or containers or devices, of the invention comprise a selection of bacterial species e.g. *Bacteroides, Firmicutes, Bacillus thuringiensis* (a bacterium capable of producing peptide antibiotics for *C. difficile*). The bacterial species may be separated by celltrifugation or plasmapharesis.

In alternative embodiments the selection of bacterial species e.g. *Bacteroides, Firmicutes, Bacillus thuringiensis* may be added to components of the compositions e.g., delivery vehicles, formulations and pharmaceutical preparations, products of manufacture, or containers or devices as fortification of concentrations comprising the bacterial species to contain wild types of bacteria.

In alternative embodiments, compositions of the invention can be formulated as fecal slurries, saline or buffered suspensions (e.g., for an enema, suspended in a buffer or a saline), in a drink (e.g., a milk, yoghurt, a shake, a flavoured drink or equivalent) for oral delivery, and the like.

In alternative embodiments, compositions of the invention can be formulated as an enema product, a spray dried product, reconstituted enema, a small capsule product, a small capsule product suitable for administration to children, a bulb syringe, a bulb syringe suitable for a home enema with a saline addition, a powder product, a powder product in oxygen deprived sachets, a powder product in oxygen deprived sachets that can be added to, for example, a bulb syringe or enema, or a spray dried product in a device that can be attached to a container with an appropriate carrier medium such as yoghurt or milk and that can be directly incorporated and given as a dosing for example for children.

In one embodiment, compositions of the invention can be delivered directly in a carrier medium via a screw-top lid wherein the fecal material is suspended in the lid and released on twisting the lid straight into the carrier medium.

In alternative embodiments methods of delivery of compositions of the invention include use of fecal slurries into the bowel, via an enema suspended in saline or a buffer, orally in a drink (e.g., a milk, yoghurt, a flavoured drink and the like), via a small bowel infusion via a nasoduodenal tube, via a gastrostomy, or by using a colonoscope. In some embodiment, there may be advantages delivering via a colonoscope to infuse as proximally as possible, and to detect any colonic pathology.

In alternative embodiments methods, fecal flora used in the composition and methods of the invention is initially derived (entirely or in part) from an individual screened or tested for a disease or infection, and/or the fecal flora is initially derived from an individual screened to have a normal, healthy or normal, representative "wild type" population of fecal flora; e.g., a normal complement of a *Bacteroides* and/or *Firmicutes*, and/or other fecal flora such as

*Bacillus thuringiensis*. In one embodiment, depending on a deficiency of a floral (e.g., bacterial) specie or species in a donor fecal material, or to achieve a desired effect, one or more additional (or "supplemental") species, e.g., *Bacteroides, Firmicutes* and/or *Bacillus thuringiensis* species, is added to (or is administered with) the delivered product either initially when the product is made, or at the time of delivery, e.g., the additional species is/are mixed in before application to the individual (e.g., patient or animal), e.g., when a powder, lyophilate, or freeze-dried composition is reconstituted for delivery; or the one or more additional (or "supplemental") species can be co-administered. These additional floral species can be directly isolated or purified from a donor, or can be expanded (cultured) for a time in vitro before addition, or can come from (be derived from) a pure culture, e.g., from an ATTC stock. For example, in some applications, e.g., to achieve a desired effect or therapeutic outcome, a delivery of an enhanced amount of one or more fecal flora (e.g., bacterial) species is used, e.g., the delivered product (e.g., an entire (or substantially entire) microbiota, or a composition comprising a complete or partial fecal flora, or a partially, substantially or completely isolated or purified fecal flora) is enhanced with (is "spiked" with") one or more additional (or "supplemental") species, e.g., *Bacteroides, Firmicutes* and/or *Bacillus thuringiensis* species, which can be directly isolated from a donor, Or can come from a pure culture, and the like.

In some embodiments, selection of the donor is of crucial importance, e.g., to avoid infecting the recipient with a separate infection or disease. In alternative embodiments the donor is tested (screened) at least for e.g., retrovirus (e.g., human immunodeficiency virus, HIV); hepatitis A, B, and/or C; cytomegalovirus; Epstein-Barr virus, detectable parasites and/or bacterial pathogens, depending on the specie of the donor and recipient, e.g., human or animal.

In alternative embodiments, the invention provides a process for preparing tea flora (e.g., an entire (or substantially entire) microbiota) for transplantation, first comprising a collection from one or more healthy (e.g., screened) donor(s). In alternative embodiments, a fresh stool is transported via a stool collection device of the invention, which in one embodiment comprises a suitably oxygen free (or substantially oxygen free) appropriate container. An exemplary suitable stool collection device 1 is shown in FIG. 1A. FIG. 1A shows an exemplary container of the invention for containing the stool and including a slot 2 for receiving the stool. The container may then be placed into a bag 3 suitably a disposable leak proof ziplock/sealing bag.

In alternative embodiments, the container can be made oxygen free by e.g., incorporating into the container a built in or clipped-on oxygen-scavenging mechanism, e.g., oxygen scavenging pellets as described e.g., in U.S. Pat. No. 7,541,091. In another embodiment, the container itself is made of an oxygen scavenging material, e.g., oxygen scavenging iron, e.g., as described by O2BLOCK™, or equivalents, which uses a purified and modified layered clay as a performance-enhancing carrier of oxygen-scavenging iron; the active iron is dispersed directly in the polymer. In one embodiment, oxygen-scavenging polymers are used to make the container itself or to coat the container, or as pellets to be added; e.g., as described in U.S. Pat. App. Pub. 2011000222, describing polymer blends having one or more unsaturated olefinic homopolymers or copolymers; one or more polyamide homopolymers or copolymers; one or more polyethylene terephthalate homopolymers or copolymers; that exhibit oxygen-scavenging activity. In one embodiment, oxygen-scavenging polymers are used to make the container itself or to coat the container, or as pellets to be added; e.g., as described in U.S. Pat. App. Pub. 20110008554, describing compositions comprising a polyester, a copolyester ether and an oxidation catalyst, wherein the copolyester ether comprises a polyether segment comprising poly(tetramethylene-co-alkylene ether). In one embodiment, oxygen-scavenging polymers are used to make the container itself or to coat the container, or as pellets to be added; e.g., as described in U.S. Pat. App. Pub. 201000255231, describing a dispersed iron/salt particle in a polymer matrix, and an oxygen scavenging film with oxygen scavenging particulates.

Alternatively, in addition to or in place of the oxygen-scavenging mechanism, the air in the container is replaced (completely or substantially) with nitrogen and/or other inert non-reactive gas or gases. In alternative embodiments, the container simulates (creates) partially, substantially or completely an anaerobic environment.

In alternative embodiments, the stool (e.g., fecal sample) is held in an aesthetically acceptable container that will not leak nor smell yet maintain an anaerobic environment. In alternative embodiments, the container is sterile before receiving the fecal flora.

In alternative embodiments, the container is maintained below room temperature, e.g., refrigerated, during most or all of its preparation, transportation and/or storage at e.g., a "stool bank" or at the site where the transplantation will take place. For example, once delivered to a "processing stool bank" it is stored in a cool room, cold container or refrigerator to minimize flora metabolism. In alternative embodiments, it is not to be frozen to prevent destruction of the bacterial cells of the stool.

In alternative embodiments, stabilizing agents such as glycerol are added to the harvested and/or stored material. In one embodiment, the stool is frozen suddenly in liquid nitrogen or any similar coolant so e.g., it can be stored for prolonged periods of time while waiting processing.

In alternative embodiments, the stool is tested for various pathogens, as noted above. In alternative embodiments, once cleared of infective agents, it is homogenized and filtered to remove large particles of matter. In alternative embodiments, it is subdivided into desired volumes, e.g., which can be between 5 cc and 3 or more liters. For example, in one embodiment, a container comprises a 50 gram (g) stool, which can be held in an appropriate oxygen resistant plastic, e.g., a metallized polyethylene terephthalate polyester film, or a metallized MYLAR™.

Figure 1B:
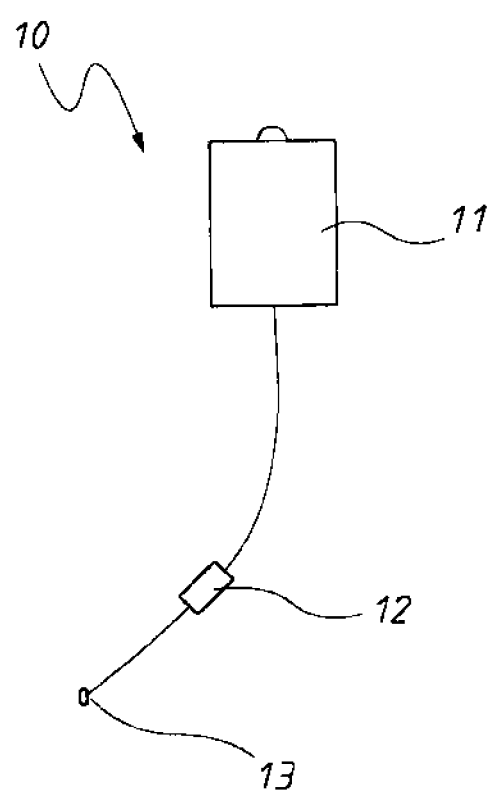

In alternative embodiments, as shown in FIG. 1B, the exemplary therapeutic vehicle (delivery system) 10 and the equipment in which the stool material is held is an intravenous-like (IV-like) giving set 11, e.g., with a hand pump 12 attached to the set. Suitably the bag 11 is metallised MYLAR™ which is impervious to gases. The hand pump 12 can allow the contents of the liquefied stool residing in the upper part of the plastic device to be easily pumped forward when the entire equipment tubing is attached by Luer lock mechanism 13 to the colonoscope biopsy channel. In this way a colonoscope or even an enteroscope will become the delivery mechanism. For this embodiment, this would usually be into the colon at any distance, and alternatively into the caecum. In alternative embodiments, the materiel is passed into a terminal ileum or even higher, as desired. In alternative embodiments, it can be infused into the duodenum or below with an enteroscope. In alternative embodiments, *C. difficile* (or the pseudo-membranous colitis associated with this infection) is ameliorated or eradicated with the infused fecal sample, or treated stool.

Figure 2:
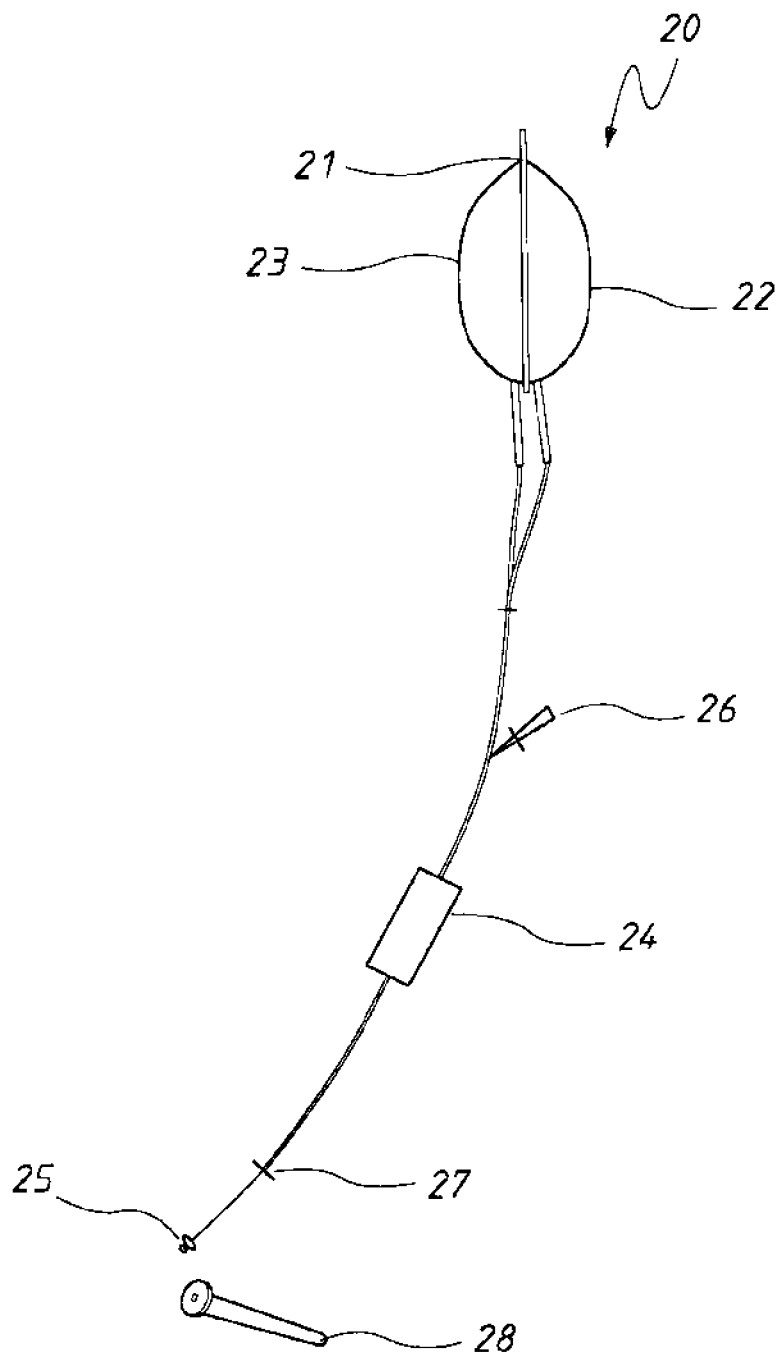
FIG. 2 illustrates an exemplary delivery device of the invention.

Another alternative embodiment is shown in FIG. 2. In this embodiment the therapeutic vehicle/delivery system 20 including an IV-like bag 21 including saline (NaCl) 22 and stool/cells 23 of the invention. In addition to the hand pump 24 and Luer lock 25, the delivery system is provided with a flushing port 26 (for flushing out the bag), a clip 27 (to prevent backwash) and an enema tip 28 with Luer lock attachment.

In alternative embodiments, the transplant material is subject to homogenization and straining. In alternative embodiments, this treated material is placed into a container, e.g., a bag, that can be attached to a nasogastric or nasoduodenal tube to allow the contents to be infused e.g., into either a stomach, duodenum or the distal jejunum. Alternatively it can be kept in a container, e.g., a bag, which can be attached to an enema tip to be given as an enema.

In alternative embodiments, to separate the non-bacterial components and produce a stable product that can be frozen or lyophilized and have a long shelf life, the stool can be homogenized and filtered from rough particulate matter. In alternative embodiments, the microscopic fiber/nonliving matter is then separated from the bacteria. Several methods can be used, including e.g., recurrent filtration with filter sizes, e.g., coming down to the size of the bacterium.

In one embodiment different filters are used to isolate the bacterial spp. This differs from the technique used for example by Williams in WO 2011/033310A1 which uses a crude technique of filtration with a gauze and is inferior to that of the present invention which utilises different sized filtration membranes to obtain the purified bacteria.

In one embodiment, a filtration procedure for filtering whole stool is suitably used to reach the highest concentration of almost 100% bacteria. In one embodiment, the filtering procedure is a two-step procedure suitably using glass fibre depth filters for initial clarification, in one embodiment, the stool is filtered under positive pressure. In one embodiment, this would be using a combination or sandwich configuration with a 30 micron PVDF filter. In one embodiment, this sandwich procedure will be filtering the product under positive pressure, Later, membrane concentration cal, in one embodiment, be used as another step to reduce to volume of the filtrate. In one embodiment, this can be done prior to freeze drying or spray drying under nitrogen cover.

Alternative membranes that can be used for filtration include, but not limited to, nylon fitters, cellulose nitrate filters, PES filters, Teflon filters, mixed cellulose Ester filters, polycarbonate filters, polpropylene filters, PVC filters or quartz litters. Various combinations of these can be used to achieve a high purity of bacteria with solids and liquid removed ready for freezing, spray-drying or lyophilisation.

For freezing, in alternative embodiments, the bacteria is held in a liquid that will prevent bursting of cells on thawing. This can include various stabilizers, e.g., glycerol and appropriate buffers, and/or ethylene in alternative embodiments, cryo-protectance uses final concentrations of stabilizer(s) of between about 20% to 60% depending in the stabilizer(s) used; this helps stabilize proteins by preventing formation of ice crystals that would otherwise destroy protein structures.

In alternative embodiments, stabilizers that help reduce destruction of living bacteria include skim milk, erythritol, arabitol, sorbitol, glucose, fructose and other polyols. Polymers such as dextran and polyethylene glycol can also be used to stabilize the faecal bacterial cells.

Mixing the appropriate amount of the bacterial flora with the stabilizer allows it to be snap frozen and kept frozen in the container that will be used to transport it to appropriate facility where the patient will have this infused after thawing.

In alternative embodiments, an entire (or substantially entire) microbiota, or an isolated and/or treated (e.g., purified or isolated) fecal material and/or flora, can be lyophilized or freeze dried, or the product can be frozen. In alternative embodiments freeze-drying allows the majority of cells to remain viable, and produces a powdered form of the product that can be gently pulverized into a powder. The powder, or lyophilized or freeze-dried flora or isolate, then can be encapsulated into a carrier, e.g., a tablet, geltab, pill or capsule, e.g., an enteric-coated capsule, or placed into oil-filled capsules for ingestion. Alternatively, the freeze-dried or lyophilized product, or powder, can be reconstituted before delivery to an individual in e.g., a fluid, e.g., a sterile fluid, such as saline, a buffer or a media such as a fluid-glucose-cellobiose agar (RGCA) media.

In alternative embodiments an entire (or substantially entire) microbiota, or an isolated and/or treated (e.g., purified or isolated) fecal material and/or flora be spray-dried. In one embodiment spray-drying is preferred over freeze-drying or lyophilising.

In alternative embodiments, the entire (or substantially entire) microbiota, or isolated and/or treated fecal material and/or flora, is supplemented with wild type bacteria which has been derived from normal animal (e.g., human) flora and/or recombinantly treated bacteria, e.g., recombinant microorganisms that can synthesize a protein, small molecule or carbohydrate that has a self-protective or ameliorative effect; or recombinant microorganisms that can self-destruct when provided with an appropriate signal, e.g., a chemical delivered by ingestion.

In alternative embodiments, the transplantation product (e.g., a composition of the invention comprising an isolated or purified fecal flora or an entire (or substantially entire) microbiota) is delivered by an infusion, e.g., through the rectum, stoma or down the upper gastrointestinal (GI) tract, or it can be used in a suppository pill, tablet or encapsulated form, e.g., with an enteric-coated graded release capsule or a tablet, e.g., with the addition of excipients. In alternative embodiments the transplantation product is administered as a suppository to give the highest concentration in the rectum.

In one embodiment, the transplantation product (e.g., a composition of the invention comprising an isolated or purified fecal flora or an entire (or substantially entire) microbiota) is stored before, during and/or after delivery to an individual, or for or during the delivery, in a fluid, e.g., a sterile fluid, such as saline, a buffer or a media such as a fluid-glucose-cellobiose agar (RGCA) media.

In alternative embodiments, the compositions and methods of the invention are used to ameliorate, stabilize, prevent and/or treat: various gastrointestinal conditions, e.g., *C. difficile* infection, *C. perfringens welchii* and other *Clostridium* infections, irritable bowel syndrome, constipation, pouchitis, Crohn's disease and microscopic colitis; neurological conditions such as Parkinson's disease, myoclonus dystonia, autism, amyotrophic lateral sclerosis and multiple sclerosis, Grand mal seizures or petit mal seizures. In one embodiment, the neurological conditions are treated by encapsulated or frozen material. In alternative embodiments, for colitis patients, recurrent administration is required to suppress and reverse the inflammatory bowel disease and irritable bowel syndrome.

In alternative embodiments, a crude collected stool is filtered and/or homogenized, and then its bacterial cells are separated (e.g., from the "crud" which contains the fiber) by plasmapheresis, centrifugation, centrifuge, column chromatography (e.g., affinity chromatography), immunoprecipitation (e.g., antibodies fixed to a solid surface, such as beads or a plate). Centrifugation, including use of a "centrifuge" (e.g., a Baxter model MEDIFUGE I215™) are processes that involve centrifugal force to separate mixtures. For "centrifugation", the densest components will then fly to the outside of the spinning plates while the rest of the components will migrate to the axis. The effect of the gravitational force will be increased by spinning the flattened product between rapidly moving glass plates. The centrifuge or centrifuge can be set up such that the stool will be diluted adequately and set on a spinning cycle and collection of cells will occur only peripherally on the centrifuge.

In alternative embodiments, wild type bacterial cells (including e.g., an entire (or substantially entire) microbiota) separated or purified e.g., by centrifugation, centrifugation, plasmapheresis and the like, are frozen using a cryoprotectant. In alternative embodiments, this material is frozen in a container, egg a bag, which can then be used to infuse through a colonoscope, naso-duodenal or nasogastric tube. In alternative embodiments, it can be delivered to a facility (e.g., a hospital pharmacy) to be kept frozen, e.g., at −20° C. or below. Alternatively the centrifuged material can be lyophilized; and can be used either in a solution, gels, geltabs, pills, capsules or tablets, or to suppositories, e.g., to be reconstituted later as an enema or infuse set through a colonoscope.

In one embodiment the cryoprotectant is trehalose. Trehalose may also function as a component upon reconstitution or as an additional agent prior to spray-drying or freeze-drying.

In alternative embodiments, solutions, gels, genet's, pills, capsules or tablets comprising compositions of the invention (e.g., isolated or purified fecal flora or an entire (or substantially entire) microbiota) can be taken long term, e.g., on a daily basis tong term, e.g., for one, two, three or four weeks or months or more, to treat, stabilize, ameliorate or prevent a chronic anchor an immune condition such as e.g., persistent infection, rheumatoid arthritis, systemic lupus erythematosus, autoimmune renal diseases, e.g., nephritis, severe obstruction, inflammatory bowel disease (IBD), irritable bowel syndrome (IBS), and other conditions set forth herein.

Preparations or Cultures of Entire Microbiota

In alternative embodiments, compositions (e.g., products of manufacture or formulations) of the invention, comprise preparations, formulations, cultures or culture extracts or isolates comprising an entire or substantially entire microbiota of an individual or specie, e.g., a human or other mammal. In alternative embodiments, the invention provides compositions and methods for preventing, decreasing the symptoms of, ameliorating stabilizing, or treating various infections, disease or conditions comprising administration of these "entire or substantially entire microbiota" preparations (e.g., cultures or culture isolates); for example, administering "entire or substantially entire microbiota" preparations for preventing, decreasing the symptoms of, ameliorating, stabilizing, or treating: spondyloarthropathy, spondylarthritis or sacrolileitis (an inflammation of one or both sacroiliac joints); a nephritis syndrome; an inflammatory or an autoimmune condition having a gut or an intestinal component such as lupus, irritable bowel syndrome (IBS or spastic colon) or a colitis such as Ulcerative Colitis or Crohn's Colitis; constipation, autism; a degenerative neurological diseases such as amyotrophic lateral sclerosis (ALS), Multiple Sclerosis (MS) or Parkinson's Disease (PD); a Myoclonus Dystonia (e.g., Steinert's disease or proximal myotonic myopathy); an autoimmune disease such as Rheumatoid Arthritis (RA) or juvenile idiopathic arthritis (JIA); Chronic Fatigue Syndrome (including benign myalgic encephalomyelitis, chronic fatigue immune dysfunction syndrome, chronic infectious mononucleosis, epidemic myalgic encephalomyelitis); obesity; hypoglycemia, pre-diabetic syndrome, type I diabetes or type II diabetes; Idiopathic thrombocytopenic purpura (ITP); an acute or chronic allergic reaction such as hives, a rash, a urticaria or a chronic urticaria; and/or insomnia or chronic insomnia, Grand mal seizures or petit mal seizures.

In alternative embodiments, the invention provides compositions and methods for administration of these "entire or substantially entire microbiota" preparations to prevent, decrease the symptoms of, ameliorate or treat various infections, diseases or conditions comprising e.g., constipation, an inflammatory bowel disease (IBD), Crohn's disease, hepatic encephalopathy, enteritis, colitis, irritable bowel syndrome (IBS), fibromyalgia (FM), chronic fatigue syndrome (CFS), depression, attention deficit/hyperactivity disorder (ADHD), multiple sclerosis (MS), systemic lupus erythematosus (SLE), travelers' diarrhea, small intestinal bacterial overgrowth, chronic pancreatitis, a pancreatic insufficiency, exposure to a poison or a toxin or for an infection, a toxin-mediated travelers diarrhea, a poisoning, a pseudomembranous colitis, a Clostridium infection, a C. perfringens welchii or a Clostridium difficile infection, a neurological condition, Parkinson's disease, myoclonus dystonia, autism, amyotrophic lateral sclerosis or multiple sclerosis, Grand mal seizures or petit real seizures.

While the invention is not limited by any particular mechanism of action, a treated or untreated fecal sample of the invention, or a composition comprising a complete or partial fecal floral sample (e.g., an entire or substantially entire microbiota") of the invention, or a partially, substantially or completely isolated or purified fecal flora of the invention, when infused into a recipient (e.g., a human or a mammal) colonize the gut. In one embodiment, these fecal floral preparations are made (e.g., isolated) by filtering human flora, and/or by spinning or centrifuging, plasmapheresis, celltrifuge, column chromatography (e.g., affinity chromatography), or immunoprecipitation and the like, to extract almost pure or substantially pure, or pure, fecal flora (e.g., "bacterial mass").

In an alternative embodiment, compositions of the invention are prepared by culturing an entire (or substantially entire) microbiota cultured simultaneously (e.g., all together without any pre-segregating out of any particular bacterial species). In one embodiment, an "entire (or substantially entire) microbiota culture" sample is formulated e.g., as a liquid, or as a freeze dried or frozen product, in one embodiment, these preparations do not contain any (or are substantially free of) non-floral material, e.g., non-absorbed components normally present in a fecal sample, e.g., a raw human stool, in one embodiment, a raw (e.g., human) stool is made into a therapeutic agent or formulation.

In one embodiment, the invention p ides methods of culturing an entire mammalian, e.g., a human, flora by taking a stool sample from a suitable donor. In one embodiment, a suitable donor is a pathogen free individual; e.g., in one aspect a sample is collected from a donor who has been classified as normal and free of any pathogens. In one embodiment, as a stand-alone therapeutic or in conjunction with other therapies, bacteria from lean donors may be used to treat obesity in obese patients.

In alternative embodiments, a culture is carried out for about 2, 3, 4, 5, 6, 7 or 8 or more days total or substantially total anaerobic conditions. Standard culturing procedures can be used using, e.g., a non-selective gut microbiota medium (GMM), and in one embodiment, incubated at (human) body temperature of about 36.8° C. An atmosphere devoid of (or substantially devoid of) oxygen and containing nitrogen, carbon dioxide and hydrogen can be used. Differing GMM can be used with varying concentrations of the composition of the GMM.

Colonies or the cultured flora are then harvested by e.g., scraping with a sterile scraper. Harvested colonies or cultured flora can be frozen e.g., in about minus 80's or below (e.g., in a freezer), using age a cryoprecipitate such as e.g., a glycerol, a cysteine or a milk. Such cultures can then be aliquoted to be used only once (as re-culturing can cause a loss of adhesions). In one embodiment, methods can comprise re-culturing e.g., in a lipid culture medium resembling a GMM. This entire medium can be frozen again using e.g., a glycerol with a cysteine; and in one embodiment, can be kept frozen or freeze-dried. This can produce between about 108 to about $10^{10}$ CFUs.

In alternative embodiments, powder, dried, frozen, freeze-dried or liquid or other forms of the cultured (e.g., human) bacteria (e.g., an entire or substantially entire microbiota") can be formulated and/or used either as an enema, a food or food supplement or formulation (e.g., added to a yoghurt, milk, drink, flavoured drink or a food), or delivered as a capsule, tablet, geltab or the like (e.g., as an enteric coated capsule) to recolonise or alternatively or therapeutically "colonize" a gut flora.

In alternative embodiments cultured bacteria is added to the culture or sample or formulation of "entire (or substantially entire) microbiota". For example, in one embodiment the first administration or the initial daily formulations comprise only an "entire microbiota" formulation; while in other embodiments the first administration or the initial daily formulations comprise both "entire microbiota" and additional cultured bacteria, e.g., cultured probiotic bacteria. In alternative embodiments, the less frequent formulations or dosages (which can be stepwise in small or larger intervals, or periodic intervals, or intervals as determined by the physician or veterinarian a; ng to rate of improvement, and the like) immense only "entire microbiota"; while in other embodiments comprise both "entire microbiota" and the additional cultured bacteria, e.g., cultured probiotic bacteria.

In alternative embodiments, to achieve a desired effect or therapeutic outcome, the additional cultured bacteria (e.g., added to the "entire microbiota") is a *Bacteroides, Firmicutes* and/or *Bacillus thuringiensis* species, which be directly isolated from a donor, or can come from a pure culture, and the like. In alternative embodiments, a delivery of an enhanced amount of one or more fecal flora (e.g., bacterial) species is used, e.g., the delivered "entire microbiota" product is enhanced with (is "spiked" with") one or more additional species, e.g., a *Bacteroides, Firmicutes* and/or *Bacillus thuringiensis* species.

Multiple or Repeated Infusions or Administrations

In alternative embodiments, compositions (e.g., products of manufacture or formulations) of the invention, including a treated or untreated fecal sample, or a partially, substantially or completely isolated or purified fecal flora, or a "culture of entire human microbiota" of the invention, or an entire (or substantially entire) microbiota or combination thereof is formulated for or calibrated for repeat or multiple delivery or infusions. In alternative embodiments of methods of the invention, the partially, substantially or completely isolated or punted fecal flora, e.g., of entire human microbiota, or an entire (or substantively entire) microbiota, or combination thereof, are delivered or administered by repeat or multiple delivery or infusions.

The invention thus provides compositions and methods for treating, stabilizing, or ameliorating gut flora infections or conditions which are difficult to permanently reverse, or for treating or ameliorating conditions characterised by gut flora infections which are difficult to permanently reverse. It has been discovered that multiple, repeated infusions can overcome gut flora infections or conditions that are difficult to permanently reverse. In alternative embodiments, in practicing the methods and/or compositions (e.g., products of manufacture or formulations) of the invention, multiple or repeated fecal flora implantations (administrations, infusions) can overcome an underlying tenacious ongoing flora infection in an individual (e.g., an animal or a patient) with e.g., pathogenic and/or foreign bacterial strains, or a chronic condition.

With inadequate elimination of the infective (e.g., pathogenic and/or fore) bacteria, the ongoing original symptoms can return. It is known that bacteria sometimes do not divide and may live in biofilms in many wet (e.g., interior) surfaces of the body. Secondly, bacteria have spores which can be more difficult to eradicate at intermittent times of sporulation. There are also dormant forms of bacteria that can be intra- and extra-cellular where they are much more difficult to eradicate—unless the dormant form is dividing. Finally, intracellular bacteria may wait until the gut wall cell in which they are housed is shed into the gut lumen re-infecting the flora. In alternative embodiments, the multiple or repeated bowel flora infusions of the methods of the invention can, and may be required, to kill or otherwise inactivate the viable (e.g., infective, pathogenic and/or foreign) bacteria which were protected inside the cell, biofilm and the like. In alternative embodiments, the multiple or repeated bowel flora infusions of the methods of the invention can, and may be required, to kill or otherwise inactivate bacterial cells that travel up crypts closer to lumen, where they are shed into the faecal stream and re-infect the individual or patient.

Additionally, in alternative embodiments, the multiple (recurrent) or repeated fecal flora implantations (administrations, infusions) of methods and/or compositions (e.g., products of manufacture or formulations) of the invention are effective for preventing, stabilizing, decreasing the symptoms of, ameliorating or treating individuals (e.g., patients) with: spondyloarthropathy, spondylarthritis or sacrolileitis (an inflammation of one or both sacroiliac joints); a nephritis syndrome; an inflammatory or an autoimmune condition having a gut or an intestinal component such as lupus, Irritable Bowel Syndrome (IBS or spastic colon) or a colitis such as Ulcerative Colitis or Crohn's Colitis; constipation, autism; a degenerative neurological diseases such as amyotrophic lateral sclerosis (ALS), Multiple Sclerosis (MS) or Parkinson's Disease (PD); a Myoclonus Dystonia (e.g., Steinert's disease or proximal myotonic myopathy); an autoimmune disease such as Rheumatoid Arthritis (RA) or juvenile idiopathic arthritis (JIA); Chronic Fatigue Syndrome (including benign myalgic encephalomyelitis, chronic fatigue immune dysfunction syndrome, chronic infectious mononucleosis, epidemic myalgic encephalomyelitis); obesity; hypoglycemia, pre-diabetic syndrome, type I diabetes or type II diabetes; Idiopathic thrombocytopenic purpura (ITP); an acute or chronic allergic reaction such as hives, a rash, a urticaria or a chronic urticaria; and/or insomnia or chronic insomnia, Grand mal seizures or petit mal seizures.

In alternative embodiments the invention is practiced (is carried out) either by use of methods or compositions of the invention, including recurrent enemas of human filtered stool, recurrent infusions through a naso-duodenal (ND) or a naso-gastric (NG) tube.

In alternative embodiments, methods or compositions of the invention formulate or use various formulations, e.g., frozen extracted stool bacterial material can be suspended as a flavoured drink or put down an ND or an NG tube or inserted as an enema.

In alternative embodiments, extracted bacteria—the 'wild types' are freeze-dried (optionally, after partial, substantial or complete purification and isolation) and formed into powder; they then can be ingested, e.g., as enteric-coated capsules, tablets, solutions and the like.

In alternative embodiments, these 'products' of the invention are initially taken, infused or administered daily, then less and less frequently, and in some embodiments, ultimately once every few weeks or monthly.

In alternative embodiments cultured bacteria a be used in addition to or with the partial, substantial or completely purified or isolated fecal flora. For example, in one embodiment the first administration or the initial daily formulations comprise only partial, substantial or completely purified or isolated fecal flora; while in other embodiments the first administration or the initial daily formulations comprise both partial, substantial or completely purified or isolated fecal flora and cultured bacteria, e.g., cultured probiotic bacteria. In alternative embodiments, the less frequent formulations or dosages (which can be stepwise in small or larger intervals, or periodic intervals, or intervals as determined by the physician or veterinarian according to rate of improvement, and the like) comprise only partial, substantial or completely purified or isolated feral flora; while in other embodiments comprise both partial, substantial or completely purified or isolated feral flora and cultured bacteria; or in other embodiments comprise only cultured bacteria, e.g., cultured probiotic bacteria.

In alternative embodiments, to achieve a desired effect or therapeutic outcome, the cultured bacteria is a *Bacteroides* and/or *Firmicutes* species and/or *Bacillus thuringiensis*, which may be directly isolated from a donor, or can come from a pure culture, and the like. In alternative embodiments, a delivery of an enhanced amount of one or more fecal flora (e.g., bacterial) species is used, e.g., the delivered product is enhanced with (is "spiked" with") one or more additional species, e.g., a *Bacteroides* and/or *Firmicutes* species and/or *Bacillus thuringiensis*.

In alternative embodiments, for adequate efficacy as to be determined by the skilled artisan, the formulations are introduced daily, or not daily—but instead recurrently for prolonged periods of time, e.g., in much higher doses. In alternative embodiments, the repeated or multiple infusion, administration or implantation protocols comprise infusions done daily for about the first 10 days, and subsequently a second daily different dosage or formulation for about 10 days, and optionally a subsequent different third daily; then optionally a different fourth daily, weekly, or monthly dosage or formulation, and then optionally maintaining different dosages or formulations for a further daily, weekly or monthly delivery or infusion until the histology reverses towards normality or other treatment parameter or goal is achieved; e.g., for the treatment of Irritable Bowel Syndrome, colitis such as Ulcerative Colitis or Crohn's Colitis, constipation, autism, degenerative neurological diseases such as Multiple Sclerosis (MS), Parkinson's Disease (PD), Myoclonus Dystonia, Rheumatoid Arthritis, Chronic Fatigue Syndrome, obesity, diabetes, type II diabetes, Idiopathic thrombocytopenic purpura (ITP), autoimmune diseases, chronic urticaria and/or insomnia or chronic insomnia, Grand mat seizures or petit mal seizures.

In alternative embodiments, the repeated or multiple infusion, administration or implantations are done with: a first formulation daily for the first 1, 2, 3, 4, 5, 6, 7, 8, 9, 10, 11, 12, 13, 14, or 15 days; a second dosage or formulation daily for a subsequent 1, 2, 3, 4, 5, 6, 7, 8, 9, 10, 11, 12, 13, 14, or 15 days or more; then optionally a third subsequent dosage or formulation daily (e.g., for a subsequent 1, 2, 3, 4, 5, 6, 7, 8, 9, 10, 11, 12, 13, 14, or 15 days or more); then optionally a fourth dosage or formulation daily or weekly (e.g., for a subsequent 1, 2, 3, 4, 5, 6, 7, 8, 9, 10, 11, 12, 13, 14, or 15 days, weeks, months or more); and optionally then maintaining weekly or monthly infusions until e.g., the histology reverses towards normality, or other appropriate parameter for treatment or recovery; e.g., for treatment of irritable Bowel Syndrome, colitis such as Ulcerative Colitis or Crohn's Colitis, constipation, autism, degenerative neurological diseases such as Multiple Sclerosis (MS), Parkinson's Disease (PD), Myoclonus Dystonia, Rheumatoid Arthritis, Chronic Fatigue Syndrome, obesity, diabetes, type II diabetes, Idiopathic thrombocytopenic purpura (FTP), autoimmune diseases, chronic urticaria and/or insomnia or chronic insomnia, Grand mal seizures or petit mal seizures. One of skill in the art, e.g., a physician or veterinarian, can assess the individual's improvement and determine the exact, appropriate dosage or frequency of administration in this "repeat administration" embodiment of the invention.

In alternative embodiments, these exemplary protocols also can be used for infusing or ingesting cultured probiotic bacteria that would be swept down the bowel in waves so as to address the issue of the biofilms spores, dormant ions and intracellular bacteria.

In summary, in alternative embodiments, the invention provides compositions and methods for treating, stabilizing, or ameliorating gut flora infections that are difficult to permanently reverse, or for treating or ameliorating conditions characterised by or related to gut flora infections that are difficult to permanently reverse or control, by multiple, repeated infusions of fecal flora, as described herein. In alternative embodiments the fecal microbiota transplant compositions and methods of the invention are effective in me more difficult conditions listed above in addition to conditions where a *Clostridium*, e.g., *C. difficile*, is the infective agent. In alternative embodiments, repeated or recurrent infusions are the key to obtaining a cure, a stabilization or a prolonged remission.

Devices for Delivering Compositions of the Invention

The invention also provides devices for delivering compositions of the invention, e.g., an exemplary delivery device is illustrated in Figures IB. In alternative embodiments, a device of the invention also can comprise or consist of:

(b) (1) a bag or container comprising an exit aperture operably connected to the proximal of a flexible tube or equivalent, wherein the bag or container is optionally made of a material impervious to as or to oxygen, and optionally the bag or container is made of a flexible material, or a polyethylene terephthalate polyester film-comprising (or a MYLAR™-comprising) material, and optionally the bag or container is an (IV-like) intravenous-like bag, and optionally the bag or container has an attachment that will allow the bag to be hung on a stand, e.g., to be positioned/hung above an endoscope, and optionally the bag or container is operably connected via an open or close valve or equivalent to a negative pressure device that can remove all gas or air from the bag, and optionally the bag or container is operably connected via an open or close valve or equivalent to a fluid source or storage container for flushing out the beg through the exit aperture, and optionally the fluid source or storage container is under positive pressure, and optionally the flexible tube or equivalent comprises at least one clip or close 25 valve or one way valve to prevent backwash of material from distal to proximal portions of the tube, or from the tube back to the bag or container;

(2) an open or close valve or equivalent or an decimator screwtop at the distal end of the flexible tube or equivalent, and optionally a Luer lock tip for attachment to a colonoscope or an endoscopic Luer lock port or equivalent, wherein optionally the Luer lock tip is built into the valve, or is separate from the valve, and optionally an enema tube tip for attachment to an enema tube or device or equivalent, in optionally the enema tube tip is built into the valve, or is separate from the valve, and optionally further comprising a safety device or safety clip to dose the distal 5 aperture in case the valve or Luer lock tip, or enema tip, is lost (flies off) under pressure; and (3) a pump, or a hand pump, for moving material in the bag or container through the flexible tube or equivalent and out the distal end or out the open or close valve or equivalent.

In alternative embodiments, a device of the invention further comprises a treated or untreated fecal flora, or a partially, substantially or completely isolated fecal flora, or a composition of the invention, e.g., a partially, substantially or completely isolated or purified fecal flora, or a composition comprising a fecal flora substantially or completely purified of non-fecal floral fecal material, and optionally further comprising an excipient, or a fluid, a saline, a buffer, a buffering agent or a media, or a fluid-glucose-cellobiose agar (RGCA) media.

In one embodiment, the invention provides a bag or container comprising a treated or untreated fecal flora, or a partially, substantially or completely isolated fecal flora, or a composition of the invention, e.g., a partially, substantially or completely isolated or purified fecal flora, or a composition comprising a fecal flora substantially or completely purified of non-fecal floral fecal material, and optionally further comprising an excipient, or a fluid, a saline, a buffer, a buffering agent or a media, or a fluid-glucose-cellobiose agar (RGCA) media, wherein the bag or container is structurally the same as or similar to a bag or container of a device of the invention, e.g., a bag or container comprising an exit aperture operably connected to the proximal end of a flexible tube or equivalent, etc., as described herein.

The invention will be further described with reference to the following examples; however, it is to be understood that the invention is not limited to such examples.

EXAMPLES

Example 1: Exemplary Methods of the Invention

One exemplary procedure of the invention involves a 5- to 10-day treatment with enemas comprising a treated or isolated fecal bacterial flora of the invention initially derived from a healthy donor. Alternatively, patients can recover after just one treatment.

In one embodiment, the best choice for donor is a close relative who has been tested for a wide array of bacterial and parasitic agents. The enemas are prepared and administered in a hospital environment to ensure alt necessary precautions. An exemplary probiotic infusion of the invention can also be administered through a nasogastric tube, delivering the bacteria directly to the small intestine. These two methods can be combined to achieve a desired result. Regular checkups should be required up to a year following the procedure.

In one embodiment an autologous fecal sample is provided by a patient before a medical treatment, and it is stored in a refrigerator, lyophilized or freeze-dried or equivalent. Should the patient subsequently develop an infection, e.g., a *C. difficile* infection, the sample is prepared (extracted) with saline and filtered. The filtrate can be freeze-dried and the resulting solid enclosed in a capsule, e.g., an enteric coated capsule, Administration of the capsules can restore the patient's own colonic flora and combat the infection, e.g., the *C. difficile*. In one embodiment, samples are delivered into the duodenum via a nasal probe.

In one embodiment, a method of the invention comprises the collection from healthy donors of fresh, human flora (stool), bringing it to a centralized institution, processing it in such a fashion that it will be given prolonged life, checking for pathogens, maintaining temperature control to reduce metabolic activity of the bacteria and controlling for oxygen-shock, developing a storage facility of the homogenized, standardized flora, and shipping the flora out to distant hospitals to treat patients with e.g. acute pseudo membranous colitis, severe *C. difficile* infection, septicemia or other comparable conditions.

In one embodiment, the product of the invention is a modified stool composition. The stool needs to be collected and promptly placed into an anaerobic container which extracts air, possibly with substances that adsorb and absorb oxygen or can be evacuated and filled with nitrogen or other gas which is either inert or will not damage anaerobic flora. It has to be held in an aesthetically acceptable container which will not leak the stool nor the gas which is producing the anaerobic situation. Once delivered to the central "bank" the stool can be stored in a cold room to slow down metabolism but not be frozen to prevent the water expansion-destruction of the bacterial cells contained in stool.

In one embodiment, either antioxidants and/or substances such as glycerol are added to help stabilize the bacteria in the cold and prevent them from becoming destroyed during storage and during transport.

In one embodiment the product is stored/contained as (in) a volume of between about 10 cc and 3 liters of stool. In one embodiment it is stored in a (as a) 300 cc container (or amount) and held in appropriate oxygen-resistant material, e.g., a plastic, an oxygen-resistant or gas impervious polyethylene terephthalate polyester film (e.g., in metalized form), or a metallized MYLAR™, or an aluminized MYLAR™, which can be attached to a pump through a giving set that with be attached to the colonoscope and administered through a colonoscope into a distal small bowel or into the upper colon/terminal ileum, to overcome *Clostridium difficile* infection.

Centre/Flora Supply Institution or "Bank"

In one embodiment, an institution functions to supply the human tiara in the following manner:

1. Stool will be collected in special containers and held cool anaerobically until it arrives at central flora processing unit.

2. In a processing unit special additives will be added including glycerol, possibly antioxidants and other special preservatives and kept cool, homogenized and dispensed into appropriate intravenous-like bags but with somewhat thicker product such as a gas impervious polyethylene terephthalate polyester film, or an aluminized MYLAR™. This will prevent oxygen being transferred, nitrogen escaping and the smell being detected by administering staff. The bags will then be kept stored at a temperature that does not allow bacteria to freeze and be ready for transport in coolers to hospitals that will be carrying out the faecal transplantation, 3. The bag will be supplied with an attached giving set, so that it does not have to be hard; by hospital staff. There will be attached to it a 'blood type' pump, with one way valve. On the (IV-like) intravenous-like bag there will be attachments that will be able to allow the bag to be hung on an IV fluids stand and be positioned/hung above the endoscope. The endoscopist will then take off the obdurator screwtop and attach to the Luer lock tip onto the endoscopic Luer lock port to be infused through the biopsy forceps channel at the tip of the colonoscope or endoscope. A safety device would be attached in case the tip flies off under pressure. The air will then be bled from the tube as the product is allowed to run down the 'giving set' with pressure mechanisms along the giving set, with air bled, and then stool only will be administered using the administering pump into the patient's colon and flushed, for example with some saline.

4. The endoscopist would then withdraw the colonoscope, turn the patient 'head down/legs up' to allow air and liquid to be absorbed and prevent the patent from undergoing defecation too early. This will allow the bacteria to re-gain temperature, start attaching themselves to the bowel wall as described e.g., by Grehan et al: J of Clinical Gastroenterology, September 2010.

A number of embodiments of the invention have been described. Nevertheless, it will be understood that various modifications may be made without departing from the spirit and scope of the invention. Accordingly, other embodiments are within the scope of the following claims.

The invention claimed is:

1. An oral capsule containing a pharmaceutical composition comprising lyophilized bacteria, wherein the lyophilized bacteria comprise a filtered bacterial population from a stool of a human donor, wherein the bacterial population is not cultured prior to lyophilization, wherein the pharmaceutical composition further comprises a cryoprotectant and an antioxidant, and wherein the filtered bacterial population is separate from fiber of said stool.

2. The oral capsule of claim 1, wherein the bacterial population comprises a non-selected fecal microbiota.

3. The oral capsule of claim 1, wherein the lyophilized bacteria further comprise a second bacterial population, wherein the second bacterial population is cultured prior to lyophilization.

4. The pharmaceutical composition of claim 3, wherein the second bacterial population is from a different source than the bacterial population.

5. The oral capsule of claim 3, wherein the second bacterial population comprises a member of the phylum Firmicutes.

6. The oral capsule of claim 3, wherein the second bacterial population comprises a member of the genus *Bacteroides*.

7. The oral capsule of claim 1, wherein the cryoprotectant is trehalose.

8. The oral capsule of claim 1, wherein the lyophilized bacteria comprises anaerobic bacteria.

9. The oral capsule of claim 1, wherein less than about 10% fecal non-flora material from the stool of a human donor are present in the pharmaceutical composition.

10. The oral capsule of claim 1, wherein less than about 10% of all fecal-originating material in the pharmaceutical composition represents fecal non-flora material.

11. The oral capsule of claim 1, wherein the antioxidant comprises cysteine.

12. The oral capsule of claim 1, wherein the filtered bacterial population is free of fiber from said stool.

13. An oral capsule containing a pharmaceutical composition comprising lyophilized bacteria, wherein the lyophilized bacteria comprise a filtered non-selected bacterial population from a stool of a human donor, wherein the pharmaceutical composition further comprises a cryoprotectant and an antioxidant, and wherein the filtered non-selected bacterial population is separate from rough particulate matter of said stool.

14. The oral capsule of claim 13, wherein the non-selected bacterial population comprises bacteria that are not cultured prior to lyophilization.

15. The oral capsule of claim 13, wherein the non-selected bacterial population is mixed with fiber.

16. The oral capsule of claim 13, wherein the human donor is a healthy human donor.

17. The oral capsule of claim 13, wherein the lyophilized bacteria further comprise a second bacterial population, wherein the second bacterial population is cultured prior to lyophilization.

18. The oral capsule of claim 13, wherein less than about 10% fecal non-flora material from the stool of a human donor are present in the pharmaceutical composition.

19. The oral capsule of claim 13, wherein less than about 10% of all fecal-originating material in the pharmaceutical composition represents fecal non-flora material.

20. The oral capsule of claim 13, wherein the antioxidant comprises cysteine.

21. The oral capsule of claim 13, wherein the filtered non-selected bacterial population is free of rough particulate matter from said stool.

22. An oral capsule containing a pharmaceutical composition comprising lyophilized bacteria, wherein the lyophilized bacteria comprise a filtered bacterial population from a stool of a human donor, wherein the bacterial population is not cultured prior to lyophilization, wherein the pharmaceutical composition further comprises a cryoprotectant and an antioxidant, and wherein the filtered bacterial population is separate from rough particulate matter of said stool.

23. The oral capsule of claim 22, wherein the bacterial population comprises a non-selected fecal microbiota.

24. The oral capsule of claim 22, wherein the lyophilized bacteria further comprise a second bacterial population, wherein the second bacterial population is cultured prior to lyophilization.

25. The pharmaceutical composition of claim 24, wherein the second bacterial population is from a different source than the bacterial population.

26. The oral capsule of claim 24, wherein the second bacterial population comprises a member of the phylum Firmicutes.

27. The oral capsule of claim 24, wherein the second bacterial population comprises a member of the genus *Bacteroides*.

28. The oral capsule of claim 22, wherein less than about 10% fecal non-flora material from the stool of a human donor are present in the pharmaceutical composition.

29. The oral capsule of claim 22, wherein less than about 10% of all fecal-originating material in the pharmaceutical composition represents fecal non-flora material.

30. The oral capsule of claim 22, wherein the cryoprotectant is trehalose.

31. The oral capsule of claim 22, wherein the antioxidant comprises cysteine.

32. The oral capsule of claim 22, wherein the filtered bacterial population is free of rough particulate matter from said stool.

* * * * *